United States Patent [19]

Nakagawa et al.

[11] Patent Number: 4,742,053

[45] Date of Patent: * May 3, 1988

[54] 3-ISOQUINOLINIOMETHYL CEPHALOSPORIN DERIVATIVES

[75] Inventors: Susumu Nakagawa; Ryosuke Ushijima, both of Okazaki; Eiichi Mano, Kariya; Norikazu Ban; Minoru Sanada, both of Okazaki, all of Japan

[73] Assignee: Banyu Pharmaceutical Co., Ltd., Tokyo, Japan

[ * ] Notice: The portion of the term of this patent subsequent to Jun. 3, 2004 has been disclaimed.

[21] Appl. No.: 796,187

[22] Filed: Nov. 8, 1985

[30] Foreign Application Priority Data

Nov. 12, 1984 [JP] Japan ................. 59-236796
Aug. 6, 1985 [JP] Japan ................. 60-171838

[51] Int. Cl.$^4$ ................. A61K 31/545; C07D 501/20
[52] U.S. Cl. ................. 514/202; 540/222
[58] Field of Search ................. 540/222; 514/202

[56] References Cited

U.S. PATENT DOCUMENTS 4,406,899 9/1983 Aburaki et al. ................. 544/22
4,457,929 7/1984 Kamachi et al. ................. 544/22
4,525,473 6/1985 Aburaki et al. ................. 514/202

FOREIGN PATENT DOCUMENTS 0121244 10/1984 European Pat. Off. .

OTHER PUBLICATIONS

Johannes Buck et al., J. Am. Chem. Soc., 60, 2101, (1938).
Grethe et al., Helv. Chim. Acta, 53, 874, (1970).
Alfred Burger, Ed., "Medicinal Chemistry," 2nd Ed., Interscience Publishers, Inc., New York, (1960), pp. 42–43.
Nakagawa et al., ICAAC Abstract, Sep. 1985.
Bobbitt et al., J. Org. Chem., 30, 2247–50, (1965).
Grethe et al., J. Org. Chem., 33, 494–503, (1968).
Johannes Buck, J. Am. Chem. Soc., 56, 1769, (1934).

*Primary Examiner*—Donald G. Daus
*Assistant Examiner*—Mark W. Noel
*Attorney, Agent, or Firm*—Oblon, Fisher, Spivak, McClelland & Maier

[57] ABSTRACT

The invention relates to an antibiotic comprising a compound having the formula:

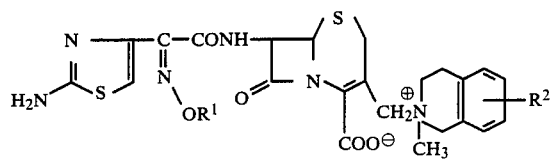

wherein $R^1$ is a straight chain, branched chain, or cyclic lower alkyl group which may be substituted by a carboxyl group, and $R^2$ designates vicinal dihydroxyl groups or diacetoxy groups; or a pharmaceutically acceptable salt, physiologically hydrolyzable ester or solvate thereof.

6 Claims, No Drawings

3-ISOQUINOLINIOMETHYL CEPHALOSPORIN DERIVATIVES

The present invention relates to cephalosporin derivatives, processes for their preparation and antibacterial agents containing them as active ingredients.

Since β-lactam antibiotics exhibit selective toxicity only against bacteria and present no substantial effects against animal cells, they have performed important roles as antibiotics with no substantial side effects in the prevention or treatment of diseases caused by the infection of bacteria.

Particularly, cephalosporin derivatives are generally stable against penicillinase and have a broad antibacterial spectrum, and thus they are frequently employed for the prevention and treatment of diseases caused by the infection of bacteria.

As published technical disclosures which describe cephalosporin derivatives having a quaternary ammonium salt substructure, there may be mentioned Japanese Unexamined patent publication Nos. 53690/1978, (GB No. 2040921) 59196/1980(U.S. Pat. No. 4,168,309), 174387/1983 (U.S. Pat. No. 4,406,899) and 198490/1983 (U.S. Pat. No. 4,457,929).

At present, cephalosporin derivatives referred to as the third generation, such as Cefotaxime [Antimicrobial Agents and Chemotherapy, 14 749 (1978)], exhibit excellent antibacterial activities against Gram-positive bacteria and Gram-negative bacteria, particularly against Enterobacteriacae.

Ceftazidime [Antimicrobial Agents and Chemotherapy, 17 876 (1980)] is the most excellent cephalosporin derivative against Gram-positive bacteria including *Pseudomonas aeruginosa* and Acinetobacter, among various cephalosporin derivatives which have been ever known.

However, the third generation cephalosporins in general have relatively poor antibacterial activities against resistant Staphylococcus having various resistant mechanisms, or against glucose non-fermentative Gram-negative rods such as resistant *Pseudomonas aeruginosa*, and *Acinetobacter calcoaceticus*.

Accordingly, a novel cephalosporin derivative having a more potent and broader antibacterial spectrum is desired for the curing of obstinate infectious diseases caused by such bacteria.

As mentioned above, cephalosporin derivatives of the so-called third generation, such as Cefotaxime, exhibit relatively poor antibacterial activities against Gram-positive bacteria, and excellent activities against Gram-negative bacteria, particularly against Enterobacteriacae, but few of them exhibit satisfactory antibacterial activities against Pseudomonads and Acinetobacters.

Accordingly, a more powerful and effective medicine is desired for the treatment of serious diseases caused by the infection of these bacteria or by the mixed infection of these bacteria and other bacteria.

The present inventors have synthesized novel cephem compounds having a 2-(2-aminothiazol-4-yl)-2-substituted oxyiminoacetyl group as a side chain at the 7-position and a 2-methyl-1,2,3,4-tetrahydro-isoquinoliniummethyl at the 3-position, and have finally found that such compounds are effective not only against Gram-positive bacteria but also against Gram-negative bacteria, particularly against glucose non-fermentative Gram-negative bacteria such as *Pseudomonas aeruginosa* and *Acinetobacter calcoaceticus* and thus have a powerful and broad antibacterial spectrum. The present invention has been accomplished on the basis of this discovery.

The present invention provides a compound having the formula:

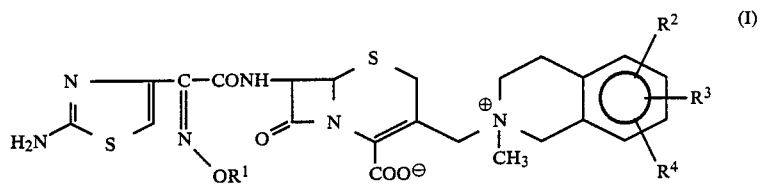

wherein $R^1$ is a straight chain, branched chain or cyclic lower alkyl group which may be substituted by a carboxyl group, and each of $R^2$, $R^3$ and $R^4$ which may be the same or different, is a hydrogen atom, a hydroxyl group, a methoxy group or an acetoxy group; or a pharmaceutically acceptable salt, physiologically hydrolyzable ester or solvate thereof Generally, the substitution of an oxyimino group may take a E-form or a Z-form in the geometrical isomerism. However, the substitution of the oxyimino group in the acylamino moiety at the 7-position of the compound of the formula I has a Z-form.

As the straight chain, branched chain or cyclic lower alkyl group which may be substituted by a carboxyl group for $R^1$ in the formula I, there may be mentioned, for instance, methyl, ethyl, n-propyl, isopropyl, n-butyl, carboxymethyl, 1-carboxy-1-methylethyl, cyclopropyl, cyclobutyl, cyclopentyl, cyclohexyl, 1-carboxy-1-cyclopropyl, 1-carboxy-1-cyclobutyl, 1-carboxy-1-cyclopentyl or 1-carboxy-1-cyclohexyl.

As the isoquinoline ring in the 2-methyl-1,2,3,4-tetrahydroisoquinoliniummethyl at the 3-position of the cephem, there may be mentioned, for instance, unsubstituted isoquinoline, 6-hydroxyisoquinoline, 7-hydroxyisoquinoline, 6-acetoxyisoquinoline, 7-acetoxyisoquinoline, 6-methoxyisoquinoline, 7-methoxyisoquinoline, 5,6-dihydroxyisoquinoline, 6,7-dihydroxyisoquinoline, 7,8-dihydroxyisoquinoline, 5,6-diacetoxyisoquinoline, 6,7-diacetoxyisoquinoline, 7,8-diacetoxyisoquinoline, 5,6-dimethoxyisoquinoline, 6,7-dimethoxyisoquinoline, 7,8-dimethoxyisoquinoline, 5,6,7-trihydroxyisoquinoline, 5,6,8-trihydroxyisoquinoline, 5,7,8-trihydroxyisoquinoline, 6,7,8-trihydroxyisoquinoline, 5,6,7-triacetoxyisoquinoline, 5,6,8-triacetoxyisoquinoline, 5,7,8-triacetoxyisoquinoline, 6,7,8-triacetoxyisoquinoline, 5,6,7-trimethoxyisoquinoline, 5,6,8-trimethoxyisoquinoline, 5,7,8-trimethoxyisoquinoline, 6,7,8-trimethoxyisoquinoline, 5,6-dihydroxy-7-methoxyisoquinoline, 5,6-dihydroxy-8-methoxyisoquinoline, 6,7-dihydroxy-5-methoxyisoquinoline, 6,7-dihydroxy-8-methoxyisoquinoline, 7,8-dihydroxy-5- methoxyisoquinoline, 7,8-dihydroxy-6-methoxyisoquinoline, 5,6-diacetoxy-7-methoxyisoquinoline, 5,6-diacetoxy-8-methoxyisoquinoline, 6,7-diacetoxy-5-methoxyisoquinoline, 6,7-diacetoxy-8-methoxyisoquinoline, 7,8-diacetoxy-5-methoxyisoquinoline, or 7,8-diacetoxy-6-methoxyisoquinoline.

The compound of the formula I can be produced by a process (Process A) which comprises reacting a compound having the formula:

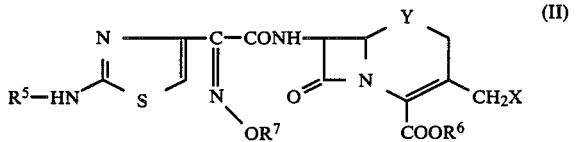

wherein $R^5$ is a hydrogen atom or an amino-protecting group, $R^6$ is a hydrogen atom or a carboxyl-protecting group, $R^7$ is a straight chain, branched chain or cyclic lower alkyl group which may be substituted by a protected carboxyl group, X is a halogen atom or a leaving group, and Y is S or SO, or a salt thereof, with an amine having the formula:

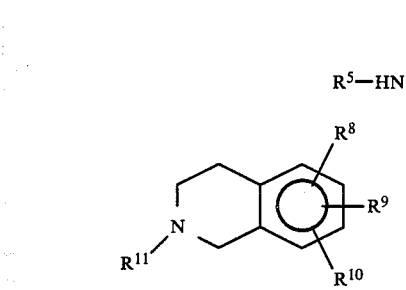

wherein each of $R^8$, $R^9$ and $R^{10}$ which may be the same or different, is a hydrogen atom, a protected or unprotected hydroxyl group, a methoxy group or an acetoxy group, and $R^{11}$ is a hydrogen atom or a methyl group, to form a compound having the formula:

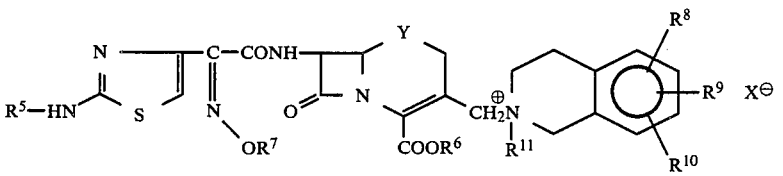

wherein $R^5$, $R^6$, $R^7$, $R^8$, $R^9$, $R^{10}$, $R^{11}$ and Y are as defined above, and $X^\ominus$ is an anion, and optionally methylating and/or reducing the compound of the formula IV, followed by the removal of the protecting groups; or a process (Process B) which comprises acylating a compound having the formula:

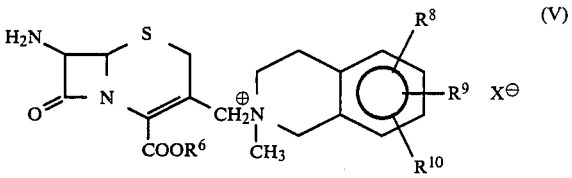

wherein $R^6$ is a hydrogen atom or a carboxyl-protecting group, each of $R^8$, $R^9$ and $R^{10}$ which may be the same or different, is a hydrogen atom, a protected or unprotected hydroxyl group, a methoxy group or an acetoxy group, and $X^\ominus$ is an anion, or a salt or silyl compound thereof, with a reactive derivative of a carboxylic acid having the formula:

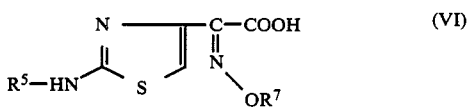

wherein $R^5$ is a hydrogen atom or an amino-protecting group, $R^7$ is a straight chain, branched chain or cyclic lower alkyl group which may be substituted by a protected carboxyl group, to form a compound having the formula:

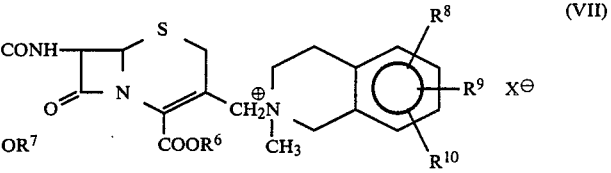

wherein $R^5$, $R^6$, $R^7$, $R^8$, $R^9$, $R^{10}$ and $X^\ominus$ are as defined above, followed by the removal of the protecting groups.

As the amino-protecting group for $R^5$ in the compound of the formula II or in the carboxylic acid derivative of the formula VI, there may be mentioned, for instance, trityl, formyl, chloroacetyl, trifluoroacetyl, t-butoxycarbonyl, trimethylsilyl or t-butyldimethylsilyl. Particularly preferred is trityl which can readily be removed by acid treatment.

As the carboxyl-protecting group for $R^6$ and $R^7$, there may be mentioned, for instance, the following protecting groups: a lower alkyl group such as t-butyl; a haloalkyl group such as 2,2,2-trichloroethyl; an alkanoyloxyalkyl group such as acetoxymethyl, propionyloxymethyl, pivaloyloxymethyl, 2-acetoxyethyl or 2-propionyloxymethyl; an alkanesulfonylalkyl group such as mesylmethyl or 2-mesylethyl; an aralkyl group such as benzyl, 4-methoxybenzyl, 4-nitrobenzyl, phenetyl, trityl, benzhydryl, bis(4-methoxyphenyl)methyl or 3,4-dimethoxybenzyl; and an alkylsilyl group such as trimethylsilyl. Particularly preferred is benzhydryl or t-butyl which can readily be removed by acid treatment.

For the substituent X in the compound of the formula II, the halogen atom may be chlorine, bromine or iodine, and the leaving group may be, for instance, acetoxy, trifluoroacetoxy, methanesulfonyloxy, trifluoromethanesulfonyloxy, phenylsulfonyloxy or p-tolylsulfonyloxy. Particularly preferred is bromine or iodine.

As the reactive derivative of a carboxylic acid of the formula VI, there may be employed, for instance, an acid halide, a mixed acid anhydride or an active ester. The acid halide of the carboxylic acid of the formula VI is obtainable by reacting the carboxylic acid of the formula VI with a halogenating agent. This acid halide-forming reaction may be conducted in an inert solvent such as methylene chloride, chloroform, dichloroethane, benzene or toluene, or a mixture thereof. As the halogenating agent, there may be employed, for instance, thionyl chloride, phosphorus trichloride, phosphorus oxychloride, phosphorus pentachloride, phosphorus tribromide, oxalyl chloride or phosgene. The halogenating agent is used in an amount of from 1 to 10 mols, preferably from 1 to 1.5 mols, per mol of the carboxylic acid of the formula VI. The reaction temperature is usually from $-40°$ to $100°$ C. preferably from $-20°$ to $+20°$ C.

The mixed acid anhydride of the carboxylic acid of the formula VI can be obtained by reacting the carboxylic acid of the formual VI with an alkyl chlorocarbonate or an aliphatic carboxylic acid chloride. The reaction is conducted in an inert solvent such as acetone, dioxane, acetonitrile, tetrahydrofuran, methylene chloride, chloroform, benzene, ethyl acetate or dimethylformamide, or a mixture thereof. The reaction is preferably conducted in the presence of a tertiary amine such as triethylamine or N-methylmorpholine. The reaction temperature is usually from $-30°$ to $20°$ C. preferably from $-15°$ to $0°$ C.

The active ester of the carboxylic acid of the formula VI is obtainable by reacting the carboxylic acid of the formula VI with preferably from 1 to 1.2 mols of an N-hydroxy compound or a phenol compound. The reaction is conducted in an inert solvent such as acetone, dioxane, acetonitrile, tetrahydrofuran, methylene chloride, chloroform, ethyl acetate or dimethylformamide, or a mixture thereof. As the N-hydroxy compound, there may be mentioned, for instance, N-hydroxysuccinimide, N-hydroxyphthalimide or 1-hydroxybenztriazole, and as the phenol compound, there may be employed, for instance, 4-nitrophenol, 2,4-dinitrophenol, trichlorophenol or pentachlorophenol. This reaciton is preferably conducted in the presence of a condensation agent such as N,N'-dicyclohexylcarbodimide. The reaction temperature is usually from $-30°$ to $40°$ C. preferably from $-10°$ to $25°$ C. The reaction time is usually from 30 to 120 minutes.

The compound of the formula II wherein Y is S, may be prepared by acylating a compound having the formula:

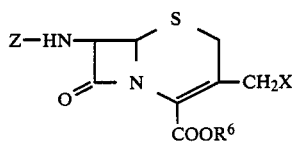

(VIII)

wherein $R^6$ and X are as defined above, and Z is a hydrogen atom or an acyl group, with an reactive derivative of a carboxylic acid of the formula VI. On the other hand, the compound of the formula II wherein Y is SO, may be obtained by oxidizing the compound of the formula II wherein Y is S. The compound of the formula II wherein X is iodine, is preferably prepared by reacting a compound of the formula II wherein X is chlorine, with sodium iodide.

The compound of the formula V is obtainable by reacting a compound of the formula VIII wherein Z is an acyl group, with an amine of the formula III wherein $R^{11}$ is a methyl group, followed by deacylation.

The compound of the formula VIII can be readily prepared from a compound having the formula:

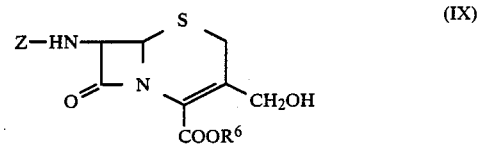

(IX)

wherein $R^6$ and Z are as defined above.

For the preparation of the compound of the formula I according to Process A, firstly, the compound of the formula II is reacted in a solvent with a free amine of the formula III or an amine salt thereof. When a hydrochloride, hydrobromide, sulfate or acetate is used as the amine salt, the reaction is usually conducted in the presence of a tertiary amine such as triethylamine in an amount sufficient for neutralization. As the solvent, there may be employed a non-aqueous organic solvent such as methylenechloride, chloroform, ether, ethyl acetate, butyl acetate, tetrahydrofuran, acetonitrile, dimethylformamide or dimethylsulfoxide, or a mixture thereof. The amine of the formula III may be silylated in the above-mentioned solvent with a silylating agent such as N,O-bistrimethylsilylacetamide. The amine of the formula III is used usually in an amount of from 1 to 5 mols per mol of the compound of the formula II. The reaction temperature is usually from $-30°$ to $35°$ C. and the reaction usually completes in from 0.2 to 10 hours.

In the case where a secondary amine of the formula III wherein $R^{11}$ is a hydrogen atom is employed, the resulting product of the formula IV may be reacted, without being isolated, i.e. as in the reaction solution, or after being separated and purified, with methyl iodide to form an ammonium compound of the formula IV. This methylation reaction may be conducted in a solvent. As such a solvent, the above-mentioned non-aqueous organic solvent is preferably employed. When the methylation reaction is conducted in the above-mentioned non-aqueous organic solvent, methyl iodide is used usually in an amount of from 1 to 30 mols, preferably from 3 to 15 mols per mol of the resulting product of the formula IV, and the reaction temperature is usually from $-30°$ to $35°$ C. The reaction is usually completed in a few hours to a few days. It is also possible to obtain the ammonium compound of the formula IV by reacting the product of the formula IV in the absence of a solvent with excess methyl iodide at a temperature of from $-20°$ to $35°$ C. for from 5 to 48 hours.

In the case where a compound of the formula II wherein Y is SO is used, the ammonium compound of the formula IV is reduced by a conventional method, for instance, by a method disclosed in e.g. Journal of Organic Chemistry, Vol. 35, 2430 (1970), Synthesis, 58

(1979) or Journal of Chemical Research, 341 (1979). For instance, the product of the formula IV is dissolved in an inert organic solvent such as acetone, methylene chloride, chloroform, tetrahydrofuran or ethyl acetate, and potassium iodide or sodium iodide is added thereto, and acetyl chloride is then dropwise added at a temperature of −40° to 0° C. The reaciton is conducted at a temperature of from −20° to −10° C. for from 1 to 5 hours to accomplish the reduction. The iodide is used in an amount of from 3.5 to 15 mols per mol of the product of the formula IV, and the acetyl chloride is used in an amount of from 1.5 to 5 mols. The compound of the formula I is obtainable by removing the protective groups from the compound thus obtained.

The method for removing the protective groups may optionally be selected from the conventional methods, depending upon the type of the protecting groups. It is preferred to employ a method of using an acid. As such an acid, there may be mentioned an inorganic or organic acid such as formic acid, trifluoroacetic acid, benzene sulfornic acid, p-toluene sulfonic acid or hydrochloric acid. Trifluoroacetic acid is preferred. In the case where trifluoroacetic acid is employed, the reaction may be accelerated by an addition of anisole. Further, this reaction may be conducted in an inert solvent, for instance, an organic solvent such as methylene chloride, ethylene chloride or benzene, or a solvent mixture thereof, preferably in methylene chloride. The reaction time is not particularly limited, and may optionally be selected depending upon the chemical nature of the starting compounds and the reaction products, or the type of the protecting groups or the manner of their removal. The reaction is preferably conducted under cooling or under a mild condition of moderate warming.

For the production of the compound of the formula I accoridng to Process B, firstly the compound of the formula V is reacted with a reactive derivative of a carboxylcc acid of the formula VI in a solvent. The reaction is conducted in an inert solvent such as water, acetone, dioxane, acetonitrile, tetrahydrofuran, methylene chloride, chloroform, benzene, ethyl acetate or dimethylformamide, or a mixture thereof. The reactive derivative of a carboxylic acid of the formula VI is used usually in an amount of from 1 to 1.5 mols per mol of the compound of the formula V. The reaction temperature is usually from −40° to 40° C. preferably from −20° to 30° C. In the case where an acid chloride or a mixed acid anhydride of the carboxylic acid of the formula VI is employed, the reaction is preferably conducted in the presence of an alkali metal carbonate or an organic amine such as trimethylamine, triethylamine or N-methylmorpholine.

After the completion of the reaction, the product of the formula VII is separated, and the protective groups are removed in the same manner as in Process A to obtain a compound of the formula I.

The compound of the formula I may be converted into a salt, physiologically hydrolyzable ester or solvate.

As the salt of the compound of the formula I, there may be mentioned a pharmaceutically acceptable common salt, for instance, a salt of an alkali metal such as sodium or potassium, an alkaline earth metal such as calcium or magnesium, an organic amine such as N,N'-dibenzylethylenediamine or procaine, an inorganic acid such as hydrochloric acid, phosphoric acid, sulfuric acid, nitric acid, perchloric acid or hdyrobromic acid, an organic acid such as acetic acid, lactic acid, propionic acid, maleic acid, fumaric acid, malic acid tartaric acid or citric acid, an organic sulfonic acid such as methanesulfonic acid, isethionic acid or p-toluenesulfonic acid, or an amino acid such as asparaginic acid or glutamic acid. As the physiologically hydrolyzable ester, there may be preferably employed an acetoxyalkyl ester such as acetoxymethylester or pivaroyloxymethyl, an alkoxycarbonyloxyalkyl ester such as 1-(ethoxycarbonyloxy)-1-ethyl, or a 5-substituted-2-oxo-1,3-dioxol-4-ylmethy ester such as 1-phthalizyl ester or 5-methyl-2-oxo-1,3-dioxol-4-ylmethyl.

The minimum inhibitory concentrations (MIC: μg/ml) of the compounds of the present invention against various microorganisms were measured by an agar plate dilution method (inoculum size: $10^6$ CFU/ml) by using Sensitivity Disk Agar (Nissui) in comparison with Cefotaxime and Ceftazidime as comparative compounds. The results are shown in Table 1.

TABLE 1

| Test microorganism | Minimum Inhibitory Concentration (μg/ml; $10^6$ CFU/ml) | | | | | | | | |
|---|---|---|---|---|---|---|---|---|---|
| | Compound of Ex. 1-B | Compound of Ex. 2-E | Compound of Ex. 3-E | Compound of Ex. 4-C | Compound of Ex. 7-D | Isomer A of Ex. 8-E | Isomer B of Ex. 8-E | Cefotaxime | Ceftazidime |
| 1. S. aureus NIHJJC-1 | 0.78 | 1.56 | 1.56 | 3.12 | 0.39 | 6.25 | 12.5 | 0.78 | 3.12 |
| 2. S. aureus JS-1 | 3.12 | 12.5 | 6.25 | 25 | 6.25 | >25 | >25 | 6.25 | 50 |
| 3. E. coli NIHJJC-2 | 0.1 | 0.78 | 0.1 | <0.05 | 0.39 | 0.2 | 0.39 | ≦0.05 | ≦0.1 |
| 4. E. coli CSH2 | 0.05 | 0.2 | 0.1 | 0.1 | 0.1 | 0.1 | 0.1 | ≦0.05 | ≦0.1 |
| 5. K. pneumoniae No. 42 | 0.2 | 1.56 | 0.39 | 0.2 | 0.78 | 0.78 | 0.78 | 0.1 | 0.39 |
| 6. P. vulgaris No. 33 | 0.2 | 1.56 | 0.2 | 0.2 | 0.39 | 0.1 | 0.1 | ≦0.05 | ≦0.1 |
| 7. P. mirabilis JY10 | 0.78 | 3.12 | 0.78 | 0.78 | 3.12 | 0.2 | 0.2 | ≦0.05 | ≦0.1 |
| 8. S. marcescens No. 16-2 | 6.25 | >25 | 12.5 | 6.25 | 6.25 | 3.12 | 3.12 | 6.25 | 1.56 |
| 9. E. cloaceae Nek 39 | 1.56 | 12.5 | 0.1 | ≦0.05 | 3.12 | 1.56 | 3.12 | 0.78 | 0.78 |
| 10. E. coli CSH | 0.2 | 1.56 | 0.78 | 1.56 | 0.2 | 0.1 | 0.2 | 0.1 | ≦0.1 |
| 11. C. freundii No. 7 | 1.56 | 12.5 | 3.12 | 6.25 | 3.12 | 1.56 | 1.56 | 0.39 | 1.56 |
| 12. P. aeruginosa AK109 | 6.25 | 25 | 0.78 | 0.1 | 6.25 | 6.25 | 3.12 | 6.25 | 1.56 |
| 13. P. aeruginosa AKR17 | >25 | >25 | 3.12 | 1.56 | >25 | 25 | >25 | >25 | >100 |
| 14. P. cepacia 23 | — | — | — | 0.78 | 6.25 | 6.25 | 6.25 | 6.25 | 0.39 |

TABLE 1-continued

| Test microorganism | | | | | | | | | |
|---|---|---|---|---|---|---|---|---|---|
| 15. A. calcoaceticus No. 14 | 25 | >25 | 0.39 | 0.39 | 25 | 25 | >25 | 25 | 6.25 |
| 16. E. coli W3630/Rms212 | 0.2 | 1.56 | 0.05 | ≦0.05 | 0.78 | 0.39 | 0.78 | ≦0.05 | 0.2 |
| 17. E. coli W3630/Rms213 | 1.56 | 3.12 | 1.56 | 1.56 | 0.78 | 0.39 | 0.78 | 0.2 | 0.2 |
| 18. E. coli ML1410/Rte16 | — | 0.78 | 0.1 | 0.1 | 0.39 | 0.2 | 0.39 | ≦0.05 | 0.2 |
| 19. E. coli C/Rms149 | 0.1 | 0.78 | 0.1 | ≦0.1 | 0.39 | 0.2 | 0.39 | ≦0.05 | 0.2 |
| 20. P. vulgaris OB1043 | 0.78 | 3.12 | 0.78 | 1.56 | 0.78 | 0.1 | 0.2 | 0.39 | ≦0.1 |
| 21. P. maltophilia IID 1275 | — | — | — | — | — | — | — | >25 | >25 |

| | Minimum Inhibitory Concentration (μg/ml; $10^6$ CFU/ml) | | | | | | | | |
|---|---|---|---|---|---|---|---|---|---|
| Test microorganism | Compound of Ex. 9 | Compound of Ex. 10 | Compound of Ex. 11 | Compound of Ex. 12 | Compound of Ex. 13 | Compound of Ex. 14-F | Compound of Ex. 15 | Cefotaxime | Ceftazidime |
| 1. S. aureus NIHJJC-1 | 0.39 | 0.39 | 6.25 | 25 | 3.12 | 12.5 | 12.5 | 0.78 | 3.12 |
| 2. S. aureus JS-1 | 12.5 | 6.25 | 25 | 50 | 12.5 | 50 | 100 | 6.25 | 50 |
| 3. E. coli NIHJJC-2 | 0.2 | 0.10 | 0.05 | 0.78 | 0.05 | 0.025 | 0.025 | ≦0.05 | ≦0.1 |
| 4. E. coli CSH2 | 0.1 | ≦0.05 | 0.39 | 1.56 | 0.05 | 0.025 | 0.025 | ≦0.05 | ≦0.1 |
| 5. K. pneumoniae No. 42 | 0.78 | 0.20 | 0.39 | 1.56 | 0.1 | 0.05 | 0.05 | 0.1 | 0.39 |
| 6. P. vulgaris No. 33 | 0.39 | 0.10 | 0.2 | 1.56 | 0.1 | 0.05 | 1.0 | ≦0.05 | ≦0.1 |
| 7. P. mirabilis JY10 | 1.56 | 0.78 | 0.39 | 0.78 | 0.39 | 0.2 | 0.1 | ≦0.05 | ≦0.1 |
| 8. S. marcescens No. 16-2 | 12.5 | 6.25 | 12.5 | 100 | 1.56 | 0.39 | 0.39 | 6.25 | 1.56 |
| 9. E. cloaceae Nek 39 | 1.56 | 0.78 | 0.025 | 1.56 | 0.006 | 0.006 | <0.006 | 0.78 | 0.78 |
| 10. E. coli CSH | 1.56 | 0.78 | 0.78 | 3.12 | 0.05 | 0.05 | 0.05 | 0.1 | ≦0.1 |
| 11. C. freundii No. 7 | 6.25 | 1.56 | 12.5 | 12.5 | 3.12 | 0.78 | 0.2 | 0.39 | 1.56 |
| 12. P. aeruginosa AK109 | 3.12 | 1.56 | 0.2 | 25 | 0.05 | 0.05 | 0.025 | 6.25 | 1.56 |
| 13. P. aeruginosa AKR17 | 25 | >25 | 6.25 | 50 | 0.2 | 0.1 | 0.05 | >25 | >100 |
| 14. P. cepacia 23 | 12.5 | 6.25 | 0.2 | 1.56 | 0.05 | 0.05 | 0.025 | 6.25 | 0.39 |
| 15. A. calcoaceticus No. 14 | >25 | 25 | 0.39 | 25 | 0.2 | 0.1 | 0.78 | 25 | 6.25 |
| 16. E. coli W3630/Rms212 | 0.2 | 0.20 | 0.025 | 0.78 | 0.0125 | 0.006 | 0.025 | ≦0.05 | 0.2 |
| 17. E. coli W3630/Rms213 | 3.12 | 1.56 | 0.78 | 3.12 | 0.05 | 0.1 | 0.025 | 0.2 | 0.2 |
| 18. E. coli ML1410/Rte16 | 0.2 | 0.10 | 0.1 | 1.56 | 0.025 | 0.025 | 0.025 | ≦0.05 | 0.2 |
| 19. E. coli C/Rms149 | 0.2 | 0.10 | 0.1 | 0.78 | 0.025 | 0.025 | 0.0125 | ≦0.05 | 0.2 |
| 20. P. vulgaris OB1043 | 0.78 | 0.39 | 1.56 | 3.12 | 0.2 | 0.1 | 0.05 | 0.39 | ≦0.1 |
| 21. P. maltophilia IID 1275 | >25 | >25 | >50 | 100 | 12.5 | 3.12 | 3.12 | >25 | >25 |

| | Minimum Inhibitory Concentration (μg/ml; $10^6$ CFU/ml) | | | | | |
|---|---|---|---|---|---|---|
| Test microorganism | Compound of Ex. 16-D | Compound of Ex. 17-E | Compound of Ex. 18-G | Compound of Ex. 19 | Cefotaxime | Ceftazidime |
| 1. S. aureus NIHJJC-1 | 1.56 | 12.5 | 25 | 25 | 0.78 | 3.12 |
| 2. S. aureus JS-1 | 12.5 | >25 | >100 | 100 | 6.25 | 50 |
| 3. E. coli NIHJJC-2 | 0.1 | ≦0.05 | 0.39 | 0.05 | ≦0.05 | ≦0.1 |
| 4. E. coli CSH2 | 0.1 | ≦0.05 | 0.78 | 0.05 | ≦0.05 | ≦0.1 |
| 5. K. pneumoniae No. 42 | 0.1 | ≦0.05 | 1.56 | 0.05 | 0.1 | 0.39 |
| 6. P. vulgaris No. 33 | 0.1 | ≦0.05 | 6.25 | 0.05 | ≦0.05 | ≦0.1 |
| 7. P. mirabilis JY10 | 0.2 | ≦0.05 | 6.25 | 0.1 | ≦0.05 | ≦0.1 |
| 8. S. marcescens No. 16-2 | 1.56 | 0.39 | 12.5 | 0.39 | 6.25 | 1.56 |
| 9. E. cloaceae Nek39 | 0.0125 | ≦0.05 | 0.1 | 0.1 | 0.78 | 0.78 |
| 10. E. coli CSH | 0.1 | ≦0.05 | 0.78 | 0.05 | 0.1 | ≦0.1 |
| 11. C. freundii No. 7 | 1.56 | 1.56 | 0.78 | 0.78 | 0.39 | 1.56 |
| 12. P. aeruginosa AK109 | 0.05 | ≦0.05 | 0.2 | 0.025 | 6.25 | 1.56 |
| 13. P. aeruginosa | 0.2 | 0.1 | 0.78 | 0.1 | >25 | >100 |

TABLE 1-continued

| | | | | | | |
|---|---|---|---|---|---|---|
| AKR17 | | | | | | |
| 14. P. cepacia 23 | 0.0125 | ≦0.05 | 0.2 | 0.0125 | 6.25 | 0.39 |
| 15. A. calco-aceticus No. 14 | 1.56 | 0.1 | 3.12 | 0.2 | 25 | 6.25 |
| 16. E. coli W3630/Rms212 | 0.0125 | ≦0.05 | 0.39 | 0.025 | ≦0.05 | 0.2 |
| 17. E. coli W3630/Rms213 | 0.1 | ≦0.05 | 0.78 | 0.025 | 0.2 | 0.2 |
| 18. E. coli ML1410/Rte16 | 0.025 | ≦0.05 | 0.2 | 0.025 | ≦0.05 | 0.2 |
| 19. E. coli C/Rms149 | 0.025 | ≦0.05 | 0.78 | 0.025 | ≦0.05 | 0.2 |
| 20. P. vulgaris OB1043 | 0.2 | ≦0.05 | 1.56 | 0.05 | 0.39 | ≦0.1 |
| 21. P. maltophilia IID 1275 | 12.5 | 1.56 | 100 | 3.12 | >25 | >25 |

The compounds of the present invention exhibit strong antibacterial activities against sensitive and resistant Gram-positive bacteria and Gram-negative bacteria, particularly against *Pseudomonas aeruginosa*, *Pseudomonas cepacia* and *Acinetobacter calcoacetic.*

Accordingly, the present invention is useful also as an antibacterial agent comprising an antibacterially effective amount of a compound of the formula I or a pharmaceutically acceptable salt, physiologically hydrolyzable ester or solvate thereof, and a pharmaceutically acceptable carrier.

The compounds of the present invention may be mixed with a carrier of solid or liquid excipient, and may be used in the form of a pharmaceutical formulation suitable for oral administration, parenteral administration or external administration. As the pharmaceutical formulations, there may be mentioned liquid formulations such as injection solutions, syrups or emulsions, solid formulations such as tablets, capsules and granules, and formulations for external application such as ointments and suppositories.

The above-mentioned formulations may contain commonly used additives such as assisting agents, stabilizers, wetting agents or emulsifying agents. For instance, injection solutions may contain a solubilizing liquid for injection such as distilled water, a physiological sodium chloride solution or a Ringer solution and a stabilizer such as methyl p-hydroxybenzoate or propyl p-hydroxybenzoate. Likewise, liquid agents such as syrups and emulsions may contain an emulsifying agents such as gum arabic, gelatin or lecithin and a surfactant such as Tween or Span in addition to sorbitol syrup, methyl cellulose, glucose, sucrose syrup, gelatin, hydroxyethyl cellulose, carboxymethyl cellulose, aluminum stearate gel, an edible oil, almond oil, coconut oil, oil ester, sorbitan monooleate, propylene glycol, glycerin, ethyl alcohol or water. For a solid formulation, lactose, sucrose, corn starch, calcium phosphate, magnesium stearate, talc, silicic acid, gum arabic, gelatin, sorbitol, traganto, polyvinylpyrrolidone, polyethylene glycol or sodium lauryl sulfate, may be employed. As the base material for ointments or suppositories, there may be employed, for instance, cacao butter, glycerides, polyethylene glycols, white vaseline, etc. A surfactant or a absorption accelerating agent may be incorporated, as the case requires.

The compound of the formula I of the present invention may be employed for the prevention and treatment of diseases caused by bacterial infections, such as infectious diseases of the respiratory system, infectiousness of the genito-urinary tract, infectious diseases of pregnant women, suppurative diseases or surgical infectious diseases. The dose may vary depending upon the age and the condition of the patient, and is usually from 1 to 100 mg/kg per day. It is preferred to administer a daily dose of from 5 to 30 mg/kg in 2 to 4 times.

Now, the present invention will be described in further detail with reference to Examples. However, it should be understood that the present invention is by no means restricted to these specific Examples.

EXAMPLE 1

(A) Benzhydryl 7-[(Z)-2-methoxyimino-2-(2-tritylaminothiazol-4-yl)acetamido]-3-(2-methyl-1,2,3,4-tetrahydro-2-isoquinolinium)methyl-3-cephem-4-carboxylate iodide 3 g (3.21 mmol) of benzhydryl 7-[(Z)-2-methoxyimino-2-(2-trithylaminothiazol-4-yl)acetamido]-3-idomethyl-3-cephem-4-carboxylate was suspended in 320 ml of diethyl ether, and 940 mg (6.38 mmol) of 2-methyl-1,2,3,4-tetrahydroisoquinoline was added at room temperature. The mixture was stirred for 15 minutes, and the precipitates were collected by filtration. To the filtrate, 500 mg (3.4 mmol) of 2-methyl-1,2,3,4-tetrahydroisoquinoline was further added, and the mixture was stirred for 40 minutes, whereupon the precipitates were collected and joined to the previous precipitates. The combined precipitates were dried to obtain 1.1 g of a mixture of $\Delta^2$- and $\Delta^3$-isomers of the above identified compound was obtained.

(B) 7-[(Z)-2-(2-aminothiazol-4-yl)-2-methoxyiminoacetamido]-3-(2-methyl-1,2,3,4-tetrahydro-2-isoquinolinium)methyl-3- cephem-4-carboxylate 1.1 g of the mixture of $\Delta^2$- and $\Delta^3$- isomers obtained in (A) was dissolved in 10 ml of methylene chloride and 1.1 ml of anisole, 10 ml of trifluoroacetic acid was dropwise added under cooling with ice. The mixture was stirred at 15° C. for 3 hours. The reaction solution was concentrated under reduced pressure, and 30 ml of ethyl acetate and 20 ml of water were added. The aqueous layer was separated, and adsorbed by HP-20 (30 ml), and then eluted with 50% methanol. The fraction containing the desired product was collected, concentrated under reduced pressure and then freeze-dried to obtain 50 mg of the desired compound (yield: 2.9%). Melting point: 163° C. (decomposed).

IR(KBr): 1765, 1660, 1610, 1530, 1345, 1035 cm$^{-1}$

NMR (D$_2$O )δ: 2.80–3.40(6H, m), 4.03(3H, s), 5.40(1H, d, J=5.4), 5.87(1H, d, J=5.4), 7.00(1H, s , 7.30–7.45(4H, m)

EXAMPLE 2

(A) Benzhydryl 7-[(Z)-2-methoxyimino-2-(2-tritylaminothiazol-4-yl)acetamido]-3-chloromethyl-3-cephem-4-carboxylate 1-oxide 2.5 g (2.97 mmol) of benzhydryl 7-[(Z)-2-methoxyimino-2-(2-tritylaminothiazol-4-yl)acetamido]-3-chloromethyl-3-cephem-4-carboxylate was dissolved in 25 ml of benzene, and 640 mg (3.27 mmol) of m-chloroperbenzoic acid was added under cooling with ice. The mixture was stirred at room temperature for 1 hour. The reaction solution was poured into ice water, and extracted with ethyl acetate. The extracted solution was washed with a 5% sodium bisulfite aqueous solution and with a saturated sodium chloride aqueous solution, then dried over anhydrous sodium sulfate and concentrated under reduced pressure, whereby the above identified compound was obtained as an oily substance.

(B) Benzhydryl 7-[(Z)-2-methoxyimino-2-(2-tritylaminothiazol-4-yl)acetamido]-3-iodomethyl-3-cephem--4-carboxylate 1-oxide The oily substance obtained in (A) was dissolved in 50 ml of acetone, and 670 mg (4.47 mmol) of sodium iodide was added. The mixture was stirred at room temperature for 30 minutes. The reaction solution was poured into ice water, and extracted with ethyl acetate. The extracted solution was washed with a 5% sodium thiosulfate aqueous solution, with water and with a saturated sodium chloride aqueous solution, then dried over anhydrous sodium sulfate and concentrated under reduced pressure, whereby an oily substance was obtained.

(C) Benzhydryl 7-[(Z)-2-methoxyimino-2-(2-tritylaminothiazol-4-yl)acetamido]-3-(6,7-dimethoxy-2-methyl-1,2,3,4-tetrahydro-2-isoquinolinium)methyl-3-cephem-4-carboxylate 1-oxide iodide The oily substance obtained in (B) was dissolved in 20 ml of dimethylformamide, and 1.23 g (5.93 mmol) of 6,7-dimethoxy-2-methyl-1,2,3,4-tetrahydroisoquinoline was added thereto. The mixture was stirred at room temperature for 3 hours. The reaction solution was poured into ice water, and extracted with methylene chloride. The extracted solution was washed sequentially with water, with a 5% sodium bisulfite aqueous solution and with a saturated sodium chloride aqueous solution, then dried over anhydrous sodium sulfate and concentrated under reduced pressure. The oily residue was treated with diethyl ether, whereby the residue was solidified. This solid was collected by filtration and dried to obtain 2.6 g of a powder (yield: 75.7%).

(D) Benzhydryl 7-[(Z)-2-methoxyimino-2-(2-tritylaminothiazol-4-yl)acetamido]-3-(6,7-dimethoxy-2-methyl-1,2,3,4-tetrahydro-2-isoquinolinium)methyl-3-cephem-4-carboxylate iodide 2.6 g (2.25 mmol) of the powder obtained in (C) was dissolved in 40 ml of acetone, and 3.8 g (25.3 mmol) of sodium iodide was added thereto. Then, 0.85 ml (11.85 mmol) of acetyl chloride was dropwise added at $-30°$ C. and then the mixture was stirred for 1 hour at a temperature of from $-30°$ to $-20°$ C. and then for 3 hours at a temperature of from $-20°$ to $-10°$ C. The reaction solution was added to an aqueous sodium methabisulfite solution cooled with ice. The precipitates were collected by filtration and washed with water. The precipitates were dissolved in methylene chloride, then washed with water and with a saturated sodium chloride aqueous solution, dried over anhydrous sodium sulfate and concentrated under reduced pressure to obtain an oily residue. The oily residue was solidified by an addition of ethyl ether, and the solid was collected by filtration and dried to obtain 2.1 g (yield: 81.9%) of a powder.

(E) 7-[(Z)-2-(2-aminothiazol-4-yl)-2-methoxyiminoacetamido]-3-(6,7-dimethoxy-2-methyl-1,2,3,4-tetrahydro-2-isoquinolinium)methyl-3-cephem-4-carboxylate 2.1 g (1.84 mmol) of the powder obtained in (D) was dissolved in 15 ml of methylene chloride and 2 ml (18.4 mmol) of anisole, and 15 ml of trifluoroacetic acid was dropwise added under cooling with ice. The mixture was stirred at the same temperature for 3 hours. The reaction solution was concentrated under reduced pressure, and 30 ml of ethyl acetate and 20 ml of water were added thereto. The aqueous layer was separated, washed twice with ethyl acetate, then adsorbed by HP-20 (50 ml) and eluted with 50% methanol. The fraction containing the desired product was collected, concentrated under reduced pressure and then freeze-dried to obtain 70 mg (yield: 6.3%) of the desired compound. Melting point: 146° C. (decomposed).

IR(KBr): 1765, 1655, 1600, 1510, 1340 cm$^{-1}$

NMR(D$_2$O)δ: 3.05–3.45(6H, m), 3.94(6H, s), 4.10(3H, s), 5.48(1H, d, J=5.5), 5.97(1H, d, J=5.5), 6.90(1H, s), 7.02(1H, s), 7.07(1H, s)

EXAMPLE 3

(A) Benzhydryl 7-[(Z)-2-methoxyimino-2-(2-tritylaminothiazol-4-yl)acetamido]-3-chloromethyl-3-cephem-4-carboxylate 1-oxide 6 g (7.14 mmol) of benzhydryl 7-[(Z)-2-methoxyimino-2-(2-tritylaminothiazol-4-yl)acetamido]-3-chloromethyl-3-cephem-4-carboxylate was dissolved in 60 ml of benzene, and 1.54 g (8.92 mmol) of m-chloroperbenzoic acid was added under cooling with ice. The mixture was stirred at room temperature for 1 hour. The reaction solution was poured into ice water, and extracted with ethyl acetate. The extract solution was washed with a 5% sodium bisulfite aqueous solution and with a saturated sodium chloride aqueous solution, then dried over anhydrous sodium sulfate and concentrated under reduced pressure to obtain an oily substance.

(B) Benzhydryl 7-[(Z)-2-methoxyimino-2-(2-tritylaminothiazol-4-yl)acetamido]-3-iodomethyl-3cephem-4-carboxylate 1-oxide The oily substance obtained in (A) was dissolved in 120 ml of acetone, and 1.6 g (10.7 mmol) of sodium iodide was added thereto. The mixture was stirred at room temperature for 30 minutes. The reaction solution was poured into ice water, and extracted with ethyl acetate. The extract solution was washed with a 5% sodium thiosulfate aqueous solution, with water and with a saturated sodium chloride aqueous solution, then dried over anhydrous sodium sulfate and concentrated under reduced pressure to obtain an oily substance.

(C) Benzhydryl 7-[(Z)-2-methoxyimino-2-(2-tritylamino-thiazol-4-yl)acetamido]-3-(6,7-dihydroxy-2-methyl-1,2,3,4-tetrahydro-2-isoquinolinium)methyl-3-cephem-4-carboxylate 1-oxide iodide A ½ amount of the oily substance obtained in (B) was dissolved in 30 ml of dimethylformamide, and 900 mg (5.03 mmol) of 6,7-dihydroxy-2-methyl-1,2,3,4-tetrahydroisoquinoline was added thereto. The mixture was stirred at room temperature for 5 hours, and then left in a refrigerator for 2 days. The reaction solution was poured into ice water, and extracted with methylene chloride. The extract solution was washed 3 times with water, and then sequentially washed with a 5% sodium bisulfite aqueous solution and with a saturated sodium chloride aqueous solution. Then, the extract solution was dried over anhydrous sodium sulfate, and concentrated under reduced pressure to obtain an oily residue. The oily residue was treated with diethyl ether, and the solidified residue was collected by filtration and dried to obtain 2.1 g (yield: 52.2%) of a powder.

(D) Benzhydryl 7-[(Z)-2-methoxyimino-2-(2-tritylaminothiazol-4-yl)acetamido]-3-(6,7-dihydroxy-2-methyl-1,2,3,4-tetrahydro-2-isoquinolinium)methyl-3-cephem-4-carboxylate iodide 2.1 g (1.86 mmol) of the powder obtained in (C) was dissolved in 40 ml of acetone, and 3.1 g (18.7 mmol) of potassium iodide was added thereto. Then, 0.67 ml (9.42 mmol) of acetyl chloride was dropwise added at −30° C. and the mixture was stirred at a temperature of from −20° to −10° C. for 90 minutes. The reaction solution was added to an aqueous metabisulfite solution cooled with ice, and the precipitates were collected by filtration and washed with water. The precipitates were dissolved in methylene chloride, then washed with water and with a saturated sodium chloride aqueous solution, dried over anhydrous sodium sulfate and concentrated under reduced pressure to obtain an oily residue. The oily residue was solidified by an addition of diethyl ether, then collected by filtration and dried to obtain 1.5 g (yield: 72.5%) of a powder.

(E) 7-[(Z)-2-(2-aminothiazol-4-yl)-2-methoxyiminoacetamido]-3-(6,7-dihydroxy-2-methyl-1,2,3,4-tetrahydro-2-isoquinolinium)methyl-3-cephem-4-carboxylate 1.5 g (1.35 mmol) of the powder obtained in (D) was dissolved in 15 ml of methylene chloride and 1.5 ml (13.8 mmol) of anisole, and 15 ml of trifluoroacetic acid was dropwise added under cooling with ice. The mixture was stirred at the same temperature for 2 hours. The reaction solution was concentrated under reduced pressure, and 30 ml of ethyl acetate and 20 ml of water were added. The aqueous layer was separated, then washed twice with ethyl acetate, adsorbed by HP-20 (50 ml) and eluted with 150 ml of cool water. The fraction containing the desired product was collected, concentrated under reduced pressure and then freeze-dried to obtain 50 mg (yield: 6.4%) of the desired compound.

Melting point: 127° C. (decomposed).

IR(KBr): 1765, 1655, 1610, 1525, 1350, 1280, 1030cm$^{-1}$
NMR(D$_2$O)δ: 2.9–3.3(6H, m), 5.40(1H, d, J=5.4), 5.90(1H, d, J=5.4), 6.72(1H, s), 6.82(1H,s), 7.04(1H, s)

EXAMPLE 4

(A) Benzhydryl 7-[(Z)-2-methoxyimino-2-(2-tritylaminothiazol-4-yl)acetamido]-3-(6,7-diacetoxy-2-methyl-1,2,3,4-tetrahydro-2-isoquinolinium)methyl-3-cephem-4-carboxylate 1-oxide iodide An oily substance of benzhydryl 7-[(Z)-2-methoxyimino-2-(2-tritylaminothiazol-4-yl)acetamido]-3-iodomethyl-3-cephem-4-carboxylate 1-oxide obtained in the same manner as in Examples 2 and 3 from 4 g (4.76 mmol) of benzhydryl 7-[(Z)-2-methoxyimino-2-(2-tritylaminothiazol-4-yl)acetamido]-3-chloromethyl-cephem-4-carboxylate, was dissolved in 20 ml of dimethylformamide, and 2.2 g (8.3 mmol) of 6,7-diacetoxy-2-methyl-1,2,3,4-tetrahydroisoquinoline was added thereto. The mixture was stirred at room temperature for 5 hours. The reaction solution was poured into ice water, and extracted with methylene chloride. The extract solution was sequentially washed with water, with a 5% sodium bisulfite aqueous solution and with a saturated sodium chloride aqueous solution. The extract solution was dried over anhydrous sodium sulfate, and concentrated under reduced pressure. The oily residue was treated with diethyl ether and solidified. The solid was collected by filtration and dried to obtain 4.9 g (yield: 84.0%) of a powder.

(B) Benzhydryl 7-[(Z)-2-methoxyimino-2-(2-tritylaminothiazol-4-yl)acetamido]-3-(6,7-diacetoxy-2-methyl-1,2,3,4-tetrahydro-2-isoquinolinium)methyl-3-cephem-4-carboxylate iodide 4.9 g (4.0 mmol) of the powder obtained in (A) was dissolved in 70 ml of acetone, and 8.7 g (52.4 mmol) of potassium iodide was added thereto. Then, 1.44 ml (20 mmol) of acetyl chloride was dropwise added at −30° C. and the mixture was stirred for 30 minutes at a temperature of from −30° to −20° C. and for 75 minutes at a temperature of from −10° to −8° C. The reaction solution was added to 320 ml of an aqueous solution containing 4.4 g of sodium metabisulfite. The precipitates were collected by filtration and washed with water. The precipitates were dissolved in methylene chloride, then washed with water, with a sodium bisulfite aqueous solution and with a saturated sodium chloride aqueous solution, dried over anhydrous sodium sulfate and concentrated under reduced pressure. The oily residue was solidified by an addition of diethyl ether, then collected by filtration and dried to obtain 3.95 g (yield: 62.7%) of a powder.

NMR(CDCl$_3$)δ: 2.22(9H, s), 2.0–2.3(2H, m), 2.4–3.4(4H, m), 3.98(3H, s), 4.2–5.0(4H, m), 5.72(1H, bd), 6.20(1H, m), 6.70(1H, s), 6.98(1H, s) 6.9–8.0(28H, m)

(C) 7-[(Z)-2-(2-aminothiazol-4-yl)-2-methoxyiminoacetamido]-3-(6,7-diacetoxy-2-methyl-1,2,3,4-tetrahydro-2-isoquinolinium)methyl-3-cephem-4-carboxylate 3.95 g (3.26 mmol) of the powder obtained in (B) was dissolved in a mixture of 20 ml of methylene chloride and 3.9 ml (35.9 mmol) of anisole, and 20 ml of trifluoroacetic acid was dropwise added under cooling with ice. The mixture was stirred at the same temperature for 2 hours. The reaction solution was concentrated under reduced pressure, and 30 ml of ethyl acetate and 30 ml of cool water were added. The aqueous layer was separated, washed twice with ethyl acetate, then adsorbed by HP-20 (70 ml) and eluted with 50% methanol. The fraction containing the desired product was collected, concentrated under reduced pressure and freeze-dried to obtain 180 mg of a crude powder. This crude powder was subjected to reversed phase column chromatography (Waters Pre Pack 500/C-18), and eluted with 5-33% methanol to obtain 18 mg (yield: 0.6%) of the desired compound and 50 mg of a mixture containing the desired compound (1:1). Melting point: 154° C. (decomposed).

IR(KBr): 1760, 1610, 1520, 1360, 1210, 1175, 1090, 1030 cm$^{-1}$

NMR($D_2O$)$\delta$: 2.38(6H, s), 2.9-3.5(6H, m), 4.03(3H, s), 5.40(1H, d, J=5.4), 5.92(1H, d, J=5.4), 7.02(1H, s), 7.16(1H, s), 7.28(1H, s)

EXAMPLE 5

(A) Benzhydryl 7-[(Z)-2-methoxyimino-2-(2-tritylaminothiazol-4-yl)acetamido]-3-(6,7-diacetoxhydro-1,2,3,4-tetrahydro-2-isoquinolin-2-yl)methyl-3-cephem-4-carboxylate 1-oxide To 760 mg (2.24 mmol) of 6,7-diacetoxy-1,2,3,4-tetrahydroisoquinoline hydrobromide, 20 ml of water and 20 ml of methylene chloride were added, and the mixture was neutralized with sodium bicarbonate powder. The organic layer was separated, and dried over anhydrous sodium sulfate to obtain a methylene chloride solution containing 6,7-diacetoxy-1,2,3,4-tetrahydroisoquinoline. To this amine solution, 1.12 g (1.18 mmol) of benzhydryl 7-[(Z)-2-methoxyimino-2-(2-tritylaminothiazol-4-yl) acetamido]-3-iodomethyl-3-cephem-4-carboxylate 1-oxide was added, and the mixture was stirred at room temperature for 1 hour. Methylene chloride was distilled off under reduced pressure, and the residue was subjected to silica gel column chromatography (methylene chloride→ 2% methanol-methylene chloride), whereby 836 mg (yield: 98%) of an amorphous powder was obtained.

NMR(CDCl$_3$)$\delta$: 2.23(6H, s), 2.4-2.9(4H, m), 3.12(1H, d, J=18), 3.2-3.5(4H, m) 4.04(3H, s), 4.05(1H, d, J=18), 4.42(1H, d, J=5), 6.08(1H, dd, J=5, 11), 6.68(1H, s), 6.72(1H, s), 6.85(1H, s), 6.96(1H, s), 7.1-7.8(25H, m)

(B) Benzhydryl 7-[(Z)-2-methoxyimino-2-(2-tritylaminothiazol-4-yl)acetamido]-3-(6,7-diacetoxy-2-methyl-1,2,3,4-tetrahydro-2-isoquinolinium)methyl-3-cephem-4-carboxylate 1-oxide iodide 817 mg (0.766 mmol) of the anhydrous powder obtained in (A) was dissolved in 8.2 ml (132 mmol) of methyl iodide, and left to stand at room temperature for 3 days in a dark place. The reaction solution was subjected to silica gel column chromatography (methylene chloride→ 2% methanol-methylene chloride→4% methanol-methylene chloride), whereby 470 mg (yield: 51%) of a powder of the above identified compound was obtained. The NMR spectrum and the thin layer chromatography of this product agreed to the compound obtained in Example 4 (A).

EXAMPLE 6

7-[(Z)-2-(2-aminothiazol-4-yl)-2-methoxyiminoacetamido]-3-(6,7-dihydroxy-2-methyl-1,2,3,4-tetrahydro-2-isoquinolinium)methyl-3-cephem-4-carboxylate 2.5 mg of the compound obtained in Example 4 (C) was suspended in 0.5 ml of methanol, and 35 μl of concentrated aqueous ammonia was added thereto. The mixture was left to stand at room temperature for 1 hour. The reaciton solution was examined by HPLC [Develosil ODS-5(10×250 mm), THF-H$_2$O) (15:85)], whereby the peak of the starting material at Rt=9.6 min. disappeared and the same peak as the compound obtained in Example 3 (E) was observed at Rt=8.0 min. The fraction of this peak was separated and freeze-dried to obtain 1 mg of the above identified compound. This compound shows a spot exhibiting antibacterial activities at Rf=0.1 in the bioautography [TLC: Merck-silica gel F254, CH$_3$CN: C$_2$H$_5$OCOCH$_3$: H$_2$O (3:1:1), E. coli NIHJ]. Further, the antibacterial spot of the starting material was at Rf=0.4. Further, this compound exhibited the same antibacterial spectrum as the compound of Example 3 (E).

EXAMPLE 7

(A) Benzhydryl 7-[(Z)-2-ethoxyimino-2-(2-tritylaminothiazol-4-yl)acetamido]-3-chloromethyl-3cephem-4-carboxylate 1-oxide 4.0 g (4.7 mmol) of benzhydryl 7-[(Z)-2-ethoxyimino-2-(2-tritylaminothiazol-4-yl)acetamido]-3-chloromethyl-3-cephem-4-carboxylate was dissolved in 40 ml of benzene, and 1.0 g (5.8 mmol) of m-chloroperbenzoic acid was added under cooling with ice. The mixture was stirred at room temperature for 40 minutes. The reaction solution was poured into ice water, and extracted with ethyl acetate. The extract solution was washed with a 5% acid sodium bisulfite aqueous solution and with a saturated sodium chloride aqueous solution, then dried over anhydrous sodium sulfate and concentrated under reduced pressure. The oily residue was solidified by an addition of n-hexane, collected by filtration and dried to obtain 3.8 g (yield: 93%) of a powder of the above identified compound.

IR(KBr): 1800, 1720, 1680, 1040, 700 cm$^{-1}$

NMR(DMSO-d$_6$)$\delta$: 1.0-1.40(3H, m), 3.30(2H, s), 3.70-4.20(4H, m), 4.30-4.70(2H, m), 5.05(1H, m), 5.90(1H, m), 6.80(1H, s), 7.00(1H, s), 7.10-7.70(25H, m), 8.75(1H, m)

(B) Benzhydryl 7-[(Z)-2-ethoxyimino-2-(2-tritylaminothiazol-4-yl)acetamido]-3-(2-methyl-1,2,3,4-tetrahydro-2-isoquinolinium)methyl-3-cephem-4-carboxylate 1-oxide iodide To 60 ml of acetone, 1.44 g (9.6 mmol) of sodium iodide was added, and the mixture was stirred for 10 minutes under cooling with ice. Then, 3.8 g (4.4 mmol) of the powder obtained in (A) was added, and the mixture was stirred for 15 minutes. The reaction solution was concentrated under reduced pressure, and ice water and ethyl acetate were added. The organic layer was separated. The organic layer was sequentially washed with a 5% sodium bisulfite aqueous solution and with a saturated sodium chloride aqueous solution, then dried over anhydrous sodium sulfate and concentrated under reduced pressure to obtain an oily 3-iodomethyl derivative. To this 3-iodomethyl derivative, 15 ml of dimethylformamide and 1.1 g (7.5 mmol) of 2-methyl-1,2,3,4-tetrahydroisoquinoline were added, and the mixture was stirred at room temperature for 40 minutes. The reaction solution was poured into ice water, and extracted with methylene chloride. The extracted solution was sequentially washed with water, with a 5% sodium bisulfite aqueous solution and with a saturated sodium chloride aqueous solution. The extract solution was dried over anhydrous sodium sulfate, and concentrated under reduced pressure to obtain an oily residue. The oily residue was treated with diethyl ether to obtain 4 g of a powder. This powder was purified by flush silica gel column chromatography (methylene chloride/methanol =20/1) to obtain a powder of 1.6 g (yield: 33.5%) of a mixture of diastereomers of the above identified compound.

IR(KBr): 1800, 1720, 1670, 1220, 1030, 750, 700 cm$^{-1}$

NMR(DMSO-d$_6$)δ: 1.0–1.35(3H, m), 4.13(2H, q, J=6), 5.17(1H, m), 6.06(1H, m), 6.78(1H, s), 6.92(1H, s), 7.00–7.70(29H, m), 8.70(1H, s), 8.95(1H, d, J=7.5)

(C) Benzhydryl 7-[(Z)-2-ethoxyimino-2-(2-tritylaminothiazol-4-yl)acetamido]-3-(2-methyl-1,2,3,4-tetrahydro-2-isoquinolinium)methyl-3-cephem-4-carboxylate 1.6 g (1.46 mmol) of the powder obtained in (B) was dissolved in 40 ml of acetone, and 2.4 g (14.4 mmol) of potassium iodide was added thereto. Then, 0.55 ml (7.7 mmol) of acetyl chloride was dropwise added at −30° C., and the mixture was stirred for 30 minutes at a temperature of from −30° to −20° C., and then for 2.5 hours at −10° C. The reaction solution was added to an aqueous sodium metabisulfite solution cooled with ice, and the precipitates thereby formed were collected by filtration and washed with water. The precipitates were dissolved in methylene chloride, washed with a saturated sodium chloride aqueous solution, then dried over anhydrous sodium sulfate and concentrated under reduced presssure to obtain an oily residue. The oily residue was solidified by an addition of ethyl ether, collected by filtration and dried to obtain a powder of 1.4 g (yield: 88.7%) of a mixture of diastereomers of the above identified compound.

IR(KBr): 1780, 1720, 1670, 1220, 1030, 750, 700 cm$^{-1}$

NMR(DMSO-d$_6$)δ: 1.0–1.40(3H, m), 4.0–4.90(8H, m), 5.43(1H, m), 5.93(1H, m), 6.80(1H, s), 6.93(1H, s), 7.0–7.70(29H, m), 9.60(1H, m)

(D) 7-[(Z)-2-(2-aminothiazol-4-yl)-2-ethoxyiminoacetamido]-3-(2-methyl-1,2,3,4-tetrahydro-2-isoquinolinium)methyl-3-cephem-4-carboxylate 1.37 g (1.27 mmol) of the powder obtained in (C) was dissolved in 10 ml of methylene chloride and 1.3 ml of anisole. Then, 9 ml of trifluoroacetic acid was dropwise added under cooling with ice, and the mixture was stirred at the same temperature for 2 hours. The reaction solution was concentrated under reduced pressure, and 10 ml of ethyl acetate and 100 ml of ice water were added thereto. The aqueous layer was separated and washed with ethyl acetate, then adsorbed by HP-20 (150 ml) and washed until the eluate became neutral. Then, 50% methanol was passed, and the fraction containing the desired product was collected, concentrated under reduced pressure and freeze-dried to obtain 340 mg (yield: 50.4%) of the desired product. Melting point: 159° C. (decomposed).

IR KBr): 1770, 1610, 1530, 1030 cm$^{-1}$

NMR(DCl-D$_2$O)δ: 1.30(3H, t, J=7.0), 2.95–3.50(7H, m), 4.30(2H, q, J=7.0), 5.35(1H, d, J=4.5), 5.80(1H, m), 7.05(1H, s), 7.10–7.40(4H, m)

EXAMPLE 8

(A) Benzhydryl 7-[(Z)-2-(1-tert-butoxycarbonyl-1-methylthoxyimino)-2-(2-trithylaminothiazol-4-yl)acetamido]-3-chloromethyl-3-cephem-4-carboxylate 1-oxide 10 g (10.3 mmol) of benzhydryl 7-[(Z)-2-(1-tertbutoxycarbonyl-1-methylethoxyimino)-2-(2-tritylaminothiazol-4-yl)acetamido]-3-chloromethyl-3-cephem-4-carboxylate was dissolved in 200 ml of methylene chloride, and 1.78 g (10.3 mmol) of m-chloroperbenzoic acid was added over a period of 10 minutes under cooling with ice. Then, the mixture was stirred for further 20 minutes. After an addition of 40 ml of a 10% sodium thiosulfate aqueous solution, the reaction solution was subjected to liquid separation. The organic layer was dried over anhydrous sodium sulfate and concentrated under reduced pressure to obtain a powder of the above identified compound.

IR(KBr): 1795, 1720, 1680, 1500, 1365, 1300, 1250, 1170, 1140, 1050 cm$^{-1}$

NMR(DMSO-d$_6$)δ: 1.36(9H, s), 1.45(6H, s), 3.9(2H, m), 4.55(2H, m), 5.1(1H, d, J=5), 6.0(1H, dd, J=5&9), 6.8(1H, s), 7.0(1H, s), 7.3(25H, brs), 8.15(1H, d, J=9), 8.7(1H, s)

(B) Benzhydryl 7-[(Z)-2-(1-tert-butxoycarbonyl-1-methylethoxyimino)-2-(2-tritylaminothiazol-4-yl(acetamido]-3-iodomethyl-3-cephem-4-carboxylate 1-oxide The compound obtained in (A) was dissolved in 200 ml of acetone, and 3.38 g (22.5 mmol) of sodium iodide was added. The mixture was stirred at room temperature for 30 minutes. To the reaction solution, 600 ml of cooled ethyl acetate and 200 ml of a cooled 10% sodium thiosulfate solution were added for liquid separation. The organic layer was dried over anhydrous sodium sulfate and concentrated under reduced pressure. The residue was purified by silica gel flush column chromatography (ethyl acetate/n-hexane=½). The fraction containing the desired product was collected, and concentrated. Diisopropyl ether was added to the residue, and 7.0 g (yield: 63.0%) of a powder of the above identified compound was collected by filtration.

IR(KBr): 1795, 1720, 1680, 1500, 1370, 1300, 1250, 1170, 1140, 1050 cm$^{-1}$

NMR(DMSO-d$_6$)δ: 1.35(9H, s), 1.45(6H, s), 3.95(2H, m), 4.45(2H, m), 5.1(1H, d, J=5), 6.0(1H, dd, J=5&9), 6.8(1H, s), 7.0(1H, s), 7.3(25H, brs), 8.15(1H, d, J=9), 8.7(1H, s)

(C) Benzhydryl 7-[(Z)-2-(1-tert-butoxycarbonyl-1-methylethoxyimino)-2-(2-tritylaminothiazol-4-yl)acetamido]-3/2-methyl-1,2,3,4-tetrahydro-2-isoquinoliniuium)methyl-3-cephem-4-carboxylate 1-oxide iodide 2 g (1.86 mmol) of the compound obtained in (B) was dissolved in 50 ml of ethyl acetate, and 300 mg (2.04 mmol) of 2-methyl-1,2,3,4-tetrahydroisoquinoline was added thereto. The mixture was stirred at room temperature for 6 hours. The reaction solution was concentrated under reduced pressure, and the residue was purified by silica gel flush column chromatography (2-3% methanol-methylene chloride), and the fraction containing the desired product was collected, and concentrated to obtain 1.20 g (yield: 52.8%) of a powder of the above identified compound.

(D) Benzhydryl 7-[((Z)-2-(1-tert-butoxycarbonyl-1-methylethoxyimino)-2-(2-tritylaminothiazol-4-yl)acetamodio]-3-(2-methyl-1,2,3,4-tetrahydro-2-isoquinolinium)methyl-3-cephem-4-carboxylate iodide 30 ml of acetone was added to 1.20 g (0.98 mmol) of the compound obtained in (C) and 810 mg (4.88 mmol) of potassium iodide, and 0.17 ml (2.39 mmol) of acetyl chloride was dropwise added at $-20°$ C. The mixture was stirred at a temperature of from $-20°$ to $-10°$ C. for 2 hours, and then after an addition of 810 mg of potassium iodide and 0.17 ml of acetyl chloride, the mixture was stirred at the same temperature for further 1.5 hours. To the reaction solution, 100 ml of methylene chloride and 100 ml of a 1% sodium metabisulfite aqueous solution > a saturated sodium chloride aqueous solution (1:1) were added, and the organic layer was dried over anhydrous sodium sulfate, and concentrated under reduced pressure to obtain a powder of the above identified compound.

IR(KBr): 1785, 1720, 1360, 1250, 1220, 1140 cm$^{-1}$ (E) 7-[(Z)-2-(2-aminothiazol-4-yl)-2-(1-carboxy-1-methylethoxyimino)acetamido]-3-(2-methyl-1,2,3,4-tetrahydro-2-isoquinolinium)methyl-3-cephem-4-carboxylate The compound obtained in (D) was dissolved in 12 ml of methylene chloride, and then 1.2 ml of anisole was added. Then, 12 ml of cooled trifluoroacetic acid was added under cooling with ice. The mixture was stirred at the same temperature for 6 hours, and the solvent was distilled off under reduced pressure. To the residue, 20 ml of ethyl acetate was added, and the solution was concentrated under reduced pressure. This operation was repeated twice, and then 150 ml of ethyl acetate and 100 ml of water were added afresh for liquid separation. To the organic layer, 100 ml of water was further added, and the aqueous layer was joined to the previous aqueous layer, and washed with 50 ml of ethyl acetate. Then, the organic solvent dissolved therein was removed under reduced pressure, and the residue was subjected to the separation and purification by reversed chromatography (Waters Pre Pack 500/C-1840 ml) (H$_2$O:200 ml, and 4% tetrahydrofuran aqueous solution: 400 ml). Then, the organic solvent was removed under reduced pressure, and the residue was freeze-dried to obtain diastereomers A and B of the above identified compound.

Compound A: 42 mg (yield: 7.0%), Melting point: 138° C. (decomposed)
IR(KBr): 1775, 1660, 1610, 1530, 1350, 1190, 1160 cm$^{-1}$
NMR(DMSO-d$_6$)δ: 1.45(6H, brs), 2.95(3H, brs), 5.2(1H, d, J=5), 5.75(1H, dd, J=5&9), 7.3(4H, brs), 9.5(1H, d, J=9)

Compound B: 78 mg (yield: 12.9%), Melting point: 140° C. (decomposed)
IR(KBr): 1175, 1660, 1610, 1530, 1340, 1185, 1155 cm$^{-1}$ NMR(DMSO-d$_6$)δ: 1.45(6H, brs), 2.95(3H, brs), 5.2(1H, d, J=5), 5.75(1H, dd, J=5&9), 7.3(4H, brs), 9.45(1H, d, J=9)

High speed liquid chromatography
Column: Develosil ODS-5 (10×250 mm)
Developer: 15% tetrahydrofuran aqueous solution
Flow rate: 2 ml/min
Detection: UV 254 nm
Retention time:
  Compound A: 5.5 min
  Compound B: 6.5 min EXAMPLES 9 to 13

In the same manner as in Example 2, the following compounds of Examples 9 to 13 were prepared.

EXAMPLE 9

7-[(Z)-2-(2-aminothiazol-4-yl)-2-methoxyiminoacetamido]-3-(6-acetoxy-2-methyl-1,2,3,4-tetrahydro-2-isoquinolinium)methyl-3-cephem-4-carboxylate (mixture of diastereomers A and B)

Melting point: 154° C. (decomposed)
IR(KBr): 1780, 1670, 1620, 1540, 1380, 1220 cm$^{-1}$
NMR(DMSO-d$_6$)δ: 2.25(3H, s), 2.8-4.7(13H, m), 3.83(3H, s), 5.15(1H, d, J=5 Hz), 5.67(1H, dd, J=5&7 Hz), 6.73(1H, s), 7.0-7.3(5H, m), 9.50(1H, d, J=7 Hz)

EXAMPLE 10

7-[(Z)-2-(2-aminothiazol-4-yl)-2-methoxyiminoacetamido]-3-(6-hydroxy-2-methyl-1,2,3,4-tetrahydro-2-isoquinolinium)methyl-3-cephem-4-carboxylate (mixture of diastereomers A and B)

Melting point: 175° C. (decomposed)
IR(KBr): 1780, 1680, 1620, 1540 cm$^{-1}$
NMR(DMSO-d$_6$)δ: 2.8-4.6(16H, m), 5.15(1H, d, J=5 Hz), 5.67(1H, dd, J=5&9 Hz), 6.63(1H, s), 6.70(1H, s), 7.20(2H, brs), 9.53(1H, d, J=9)

EXAMPLE 11

7-[(Z)-2-(2-aminothiazol-4-yl)-2-methoxyiminoacetamido]-3-(5,6-dihydroxy-2-methyl-1,2,3,4-tetrahydro-2-isoquinolinium)methyl-3-cephem-4-carboxylate (mixture of diastereomers A and B)

Melting point: 166° C. (decomposed)
IR(KBr): 1780, 1680, 1620, 1200, 1140, 1050 cm$^{-1}$
NMR(DMSO-d$_6$)δ: 2.96(3H, brs), 3.2-4.9(13H, m), 5.29(1H, d, J=5 Hz), 5.87(1H, d, J=5&9 Hz), 6.45(1H, m), 6.73(1H, s), 6.9-7.3(2H, m), 9.60(1H, d, J=9 Hz)

EXAMPLE 12

7-[(Z)-2-(2-aminothiazol-4-yl)-2-methoxyiminoacetamido]-3-(2-methyl-1,2,3,4-tetrahydro-6,7,8-trihydroxy-2-isoquinolinium)methyl-3-cephem-4-carboxylate (mixture of diastereomers A and B)

Melting point: 182° C. (decomposed)
IR(KBr): 1780, 1670, 1620, 1540, 1480 cm$^{-1}$
NMR(DMSO-d$_6$)δ: 2.6-4.5(16H, m), 5.17(1H, m), 5.68(1H, m), 6.20(1H, s), 6.73(1H, s), 7.20(2H, brs), 9.55(1H, d, J=9 Hz)

EXAMPLE 13

7-[(Z)-2-(2-aminothiazol-4-yl)-2-isopropoxyiminoacetamido]-3-(6,7-dihydroxy-2-methyl-1,2,3,4-tetrahydro-2-isoquinolinium)methyl-3-cephem-4-carboxylate (mixture of diastereomers A and B)

Melting point: 174° C. (decomposed)
IR(KBr): 1780, 1620, 1540, 1390, 1360 cm$^{-1}$ NMR(DMSO-d$_6$)δ: 1.23(6H, d, J=6 Hz), 2.90(3H, brs), 3.0–4.6(11H, m), 5.17(1H, d, J=5 Hz), 5.67(1H, dd, J=5&9Hz), 6.51(1H, s), 6.63(1H, s), 6.70(1H, s), 7.20(2H, brs), 9.45(1H, d, J=9 Hz)

EXAMPLE 14

(A) Benzhydryl 7-[(Z)-2-(benzhydryloxycarbonylmethoxyimino)-2-(2-tritylaminothiazol-4-yl)acetamido]-3-chloromethyl-3-cephem-4-carboxylate 1-oxide 23.4 g (22.3 mmol) of benzhydryl 7-[(Z)-2-(benzhydryloxycarbonylmethoxyimino)-2-(2-tritylaminothiazol-4-yl)acetamido]-3-chloromethyl-3-cephem-4-carboxylate was dissolved in 500 ml of methylene chloride, and 4.8 g (22.3 mmol) of m-chloroperbenzoic acid was added over a period of 10 minutes under cooling with ice. The mixture was stirred for further 20 minutes. After an addition of 150 ml of a 10% sodium thiosulfate aqueous solution, the reaction solution was subjected to liquid separation. The organic layer was washed with a 5% sodium bicarbonate aqueous solution, then dried over anhydrous sodium sulfate, and concentrated under reduced pressure to obtain a powder of the above identified compound (the powder was used to the subsequent reaction without purification).

IR(KBr): 1800, 1730, 1680, 1520, 1490, 1450, 1375, 1250, 1180, 1090, 1060, 1010, 750, 700 cm$^{-1}$

(B) Benzhydryl 7-[(Z)-2-(benzhydryloxycarbonylmethoxyimino)-2-(2-tritylaminothiazol-4-yl)acetamido]-3-iodomethyl-3-cephem-4-carboxylate 1-oxide The compound obtained in (A) was dissolved in 380 ml of acetone, and 7.4 g (49 mmol) of sodium iodide was added thereto. The mixture was stirred at room temperature for 30 minutes. To the reaction solution, 300 ml of a 10% sodium thiosulfate aqueous solution and 1150 ml of ethyl acetate were added for liquid separation. The organic layer was dried over anhydrous sodium sulfate, and concentrated under reduced pressure. The residue was purified by silica gel flush column chromatography (ethyl acetate/n-hexane=1/1) to obtain 22.4 g (yield based on the previous step: 86.7%) of a powder of the above identified compound.

IR(KBr): 1795, 1725, 1685, 1520, 1495, 1450, 1370, 1290, 1230, 1180, 1085, 1060, 750, 700 cm$^{-1}$

NMR(DMSO-d$_6$)δ: 3.9(2H, brs), 4.5(2H, m), 4.9(2H, brs), 5.08(1H, d, J=5 Hz), 5.93(1H, dd, J=5&8 Hz), 6.87(1H, s), 6.92(1H, s), 7.0(1H, s), 7.35(36H, m), 8.85(2H, m)

(C) Benzhydryl 7-[(Z)-2-(benzhydryloxycarbonylmethoxyimino)-2-(2-tritylaminothiazol-4-yl)acetamide]-3-(6,7-cephem-dihydroxy-1,2,3,4-tetrahydroisoquinolin-2-yl)methyl-4-carboxylate 1-oxide 4 g (3.4 mmol) of the compound obtained in (B) and 1.27 g (5.2 mmol) of 6,7-dihydroxy-1,2,3,4-tetrahydroisoquinoline hydrobromide were dissolved in 15 ml of dimethylformamide, and 0.71 ml (5.1 mmol) of triethylamine was added thereto at room temperature. The mixture was stirred at the same temperature for 2 hours. The reaction solution was concentrated under reduced pressure. The residue was purified by silica gel column chromatography (2% methanol-chloroform) to obtain 3.5 g (yield: 84%) of the above identified compound.

IR(KBr): 1800, 1740, 1660, 1530 cm$^{-1}$

NMR(DMSO-d$_6$)δ: 2.3–2.7(4H, m), 3.0–3.5(6H, m), 4.37(1H, d, J=6.0 Hz), 4.87(2H, brs), 6.03(1H, m), 6.30(1H, s), 6.47(1H, s), 6.70(1H, s), 6.88(1H, s), 6.95(1H, s), 7.1–7.5(35H, m)

(D) Benzhydryl 7-[(Z)-2-(benzhydryloxycarbonylmethoxyimino)-2-(2-tritylaminothiazol-4-yl)acetamido]-3-(6,7-dihydroxy-2-methyl-1,2,3,4-tetrahydroisoquinolinium)methyl-3-cephem-4-carboxylate 1-oxide iodide 3.5 g of the compound obtained in (C) was dissolved in 20 ml (321 mmol) of methyl iodide, and the solution was stirred at room temperature for 15 hours. The reaction solution was concentrated under reduced pressure. The residue was purified by silica gel column chromatography (2–5% methanol-chloroform) to obtain 2.7 g (yield: 69%) of the above identified compound.

IR(KBr): 1800, 1690, 1640, 1620, 1530 cm$^{-1}$

NMR(DMSO-d$_6$)δ: 2.6–3.0(3H, m), 3.0–3.7(6H, m), 3.9–4.5(4H, m), 4.83(2H, brs), 5.40(1H, d, J=4.5 Hz), 5.93(1H, m), 6.47(1H, s), 6.61(1H, s), 6.77(1H, s), 6.88(1H, s), 7.1–7.6(35H, m)

(E) Benzhydryl 7-[(Z)-2-(benzhydryloxycarbonylmethoxyimino)-2-(2-tritylaminothiazol-4-yl)acetamido]-3-(6,7-dihydroxy-2-methyl-1,2,3,4-tetrahydroisoquinolinium)methyl-3-cephem-4-carboxylate iodide 2.7 g (2.0 mmol) of the compound obtained in (D) was dissolved in 50 ml of acetone, and 3.35 g (20.2 mmol) of potassium iodide was added thereto. Then, 0.72 ml (10 mmol) of acetyl chloride was added at −20° C., and the mixture was stirred at −20° C. for 30 minutes and at −10° C. for 3.5 hours. The reaction solution was poured into a 2% sodium metabisulfite aqueous solution, and the precipitates were collected by filtration. The precipitates were dissolved in chloroform, washed with a saturated sodium chloride aqueous solution, and then dried over anhydrous sodium sulfate. The solvent was distilled off under reduced pressure to obtain 2.3 g (yield: 86%) of the above identified compound.

NMR(DMSO-d$_6$)δ: 2.6–2.9(3H, m), 3.1–3.8(6H, m), 4.0–4.6(4H, m), 5.17(1H, m), 6.07(1H, m), 6.43(1H, s), 6.60(1H, s), 6.85(1H, s), 6.88(1H, s), 7.1–7.6(35H, m)

(F) 7-[(Z)-2-(2-aminothiazol-4-yl)-2-carboxymethoxyiminoacetamido]-3-(6,7-dihydroxy-2-methyl-1,2,3,4-tetrahydro-2-isoquinolinium)methyl-3-cephem-4-carboxylate (mixture of diastereomers A and B)

2.2 g (1.66 mmol) of the compound obtained in (E) was dissolved in 10 ml of methylene chloride and 2.2 ml of anisole, and 15 ml of trifluoroacetic acid was dropwise added under cooling with ice. The mixture was stirred for 2 hours. The reaction solution was concentrated under reduced pressure, and ethyl acetate and water were added to the residue. The aqueous layer was purified by reversed chromatography (Waters Pre Pack 500/C-18: 2% tetrahydrofuran-water). The fraction containing the desired product was collected, and freeze-dried to obtain 180 mg (yield: 17.5%) of the above identified compound.

Melting point: 179° C. (decomposed)

IR(KBr): 1780, 1620, 1540, 1390, 1360, 1280 cm$^{-1}$

NMR(DMSO-d$_6$)δ: 2.93(3H, brs), 3.0–4.7(10H, m), 4.57(2H, brs), 5.60(2H, brs), 5.20(1H, d, J=5 Hz), 5.53(1H, s), 5.73(1H, m), 6.63(1H, s), 6.83(1H, s), 7.23(2H, brs), 9.80(1H, d, J=9 Hz)

EXAMPLE 15

In the same manner as in Example 14, 7-[(Z)-2-(2-aminothiazol-4-yl)-2-(1-carboxy-1-methylethoxyimino)acetamido]-3-(6,7-dihydroxy-2-methyl-1,2,3,4-tetrahydro-2-isoquinolinium)methyl-3-cephem-4-carboxylate (mixture of diastereomers A and B)

Melting point: 184° C. (decomposed)

IR(KBr): 1780, 1620, 1540, 1390, 1360, 1280, 1200, 1160 cm$^{-1}$

NMR(DMSO-d$_6$)δ: 1.50(6H, s), 2.93(3H, brs), 3.0–4.7(10H, m), 5.22(1H, d, J=5 Hz), 5.75(1H, dd, J=5&9 Hz), 6.53(1H, s), 6.65(1H, s), 6.75(1H, s), 9.55(1H, d, J=9 Hz)

EXAMPLE 16

(A) Benzhydryl 7-[(Z)-2-cyclopentyloxyimino-2-(2-tritylaminothiazol-4-yl)acetamido]-3-(6,7-dihydroxy-1,2,3,4-tetrahydroisoquinolin-2-yl)3-cephem-4-carboxylate 1-oxide 3.5 g (3.49 mmol) of benzhydryl 3-iodomethyl-7-[(Z)-2-cyclopentyloxyimino-2-(2-tritylaminothiazol-4-yl)acetamido]-3-cephem-4-carboxyliate was dissolved in 15 ml of dimethylformamide, and 1.28 g (5.2 mmol) of 6,7-dihydyroxy-1,2,3,4-tetrahydroisoquinoline hydrobromide and 0.73 ml (5.2 mmol) of triethylamine were added at room temperature. The reaction solution was stirred for 1 hour, and dimethylformamide was distilled off under reduced pressure. Water and chloroform were added to the residue, and the organic layer was washed with a saturated sodium chloride aqueous solution. Then, the organic layer was dried over anhydrous sodium sulfate, and concentrated under reduced pressure. The residue was subjected to silica gel column chromatography (2–5% methanol-chloroform) to obtain 3 g (yield: 82.6%) of the above identified compound.

IR(KBr): 1810, 1730, 1660, 1620, 1530 cm$^{-1}$

NMR(DMSO-d$_6$)δ: 1.4–1.9(8H, m), 2.3–3.4(10H, m), 4.65(1H, m), 5.07(1H, d, J=4.5 Hz), 5.85(1H, dd, J=4.5 & 7 Hz), 6.31(1H, s), 6.42(1H, s), 6.77(1H, s), 6.97(1H, s), 7.15–7.5(25H, brs), 8.4–8.8(3H, m)

(B) Benzhydryl 7-[(Z)-2-cyclopentyloxyimino-2-(2-tritylaminothiazol-4-yl)acetamido]-3-(6,7-dihydroxymethyl-1,2,3,4-tetrahydro-2-isoquinolinium)methyl-3-cephem-4-carboxylate 1-oxide iodide 3 g ((2.3 mmol) of the compound obtained in (A) was dissolved in 20 ml (321 mmol) of methyl iodide, and the solution was stirred at room temperature for 19 hours. The reaction solution was concentrated under reduced pressure, and ether was added to the residue, whereby 2.5 g (yield: 73.3%) of a powder of the above identified compound was obtained.

NMR(DMSO-d$_6$)δ: 1.4–1.9(8H, m), 2.6–4.4(13H, m), 4.63(1H, m), 5.13(1H, m), 5.93(1H, m), 6.43(1H, s), 6.60(1H, s), 6.78(1H, s), 7.12(1H, s), 7.3–7.5(25H, brs), 8.80(2H, m)

(C) Benzhydryl 7-[(Z)-2-cyclopentyloxyimino-2-(2-tritylaminothiazol-4-yl)acetamido]-3-(6,7-dihydroxy-2-methyl-1,2,3,4-tetrahydro-2-isoquinolinium)methyl-3-cephem-4-carboxylate iodide 2.5 g (2.1 mmol) of the compound obtained in (B) was dissolved in 50 ml of acetone, and 3.5 g (21 mmol) of potassium iodide was added thereto. Then, 0.75 ml (10.5 mmol) of acetyl chloride was dropwise added at −20° C. The reaction solution was stirred at −10° C. for 5 hours. The reaction solution was poured into a 2% sodium metabisulfite aqueous solution, and the precipitates were collected by filtration. The precipitates were dissolved in chloroform, and washed with a saturated sodium chloride aqueous solution. Then, the organic layer was dried over anhydrous sodium sulfate. The solvent was distilled off under reduced pressure to obtain 2.2 g (yield: 89%) of the above identified compound.

IR(KBr): 1800, 1730, 1680, 1620, 1530, 1450, 1360 cm$^{-1}$

NMR(DMSO-d$_6$)δ: 1.2–2.0(8H, m), 5.43(1H, m), 5.90(1H, m), 6.50(1H, s), 6.63(1H, s), 6.77(1H, s), 6.95(1H, s), 7.0–7.7(25H, brs), 9.55(1H, m)

(D) 7-[(Z)-2-(2-aminothiazol-4-yl)-2-cyclopentyloxyiminoacetamido]-3-(6,7-dihydroxy-2-methyl-1,2,3,4-tetrahydro-2-isoquinolinium)methyl-3-cephem-4-carboxylate 2.1 g (1.8 mmol) of the compound obtained in (C) was dissolved in 10 ml of methylene chloride and 2 ml of anisole, and 16 ml of trifluoroacetic acid was dropwise added under cooling. The mixture was stirred at the same temperature for 2 hours. The reaction solution was concentrated under reduced pressure, and ether was added to the residue to obtain the precipitates. To the precipitates, 200 ml of water was added, and insoluble matters were removed. The filtrate was purified by reversed column chromatography (Waters PrePack 500/C-18: 15–40% methanol-water). The fraction containing the desired product was collected and freeze-dried to obtain 220 ml (yield: 19.5%) of the above identified compound.

Melting point: 178° C. (decomposed)

IR(KBr): 1780, 1670, 1620, 1540, 1390, 1360 cm$^{-1}$

NMR(DMSO-d$_6$)δ: 1.3–1.9(8H, m), 2.90(3H, brs), 3.0–4.8(10H, m), 4.65(1H, m), 5.17(1H, d, J=4.5 Hz), 5.65(1H, dd, J=4.5&9 Hz), 6.51(1H, s), 6.62(1H, s), 6.68(1H, s)

EXAMPLE 17

(A) Benzhydryl 7-[(Z)-2-(1-tert-butoxycarbonyl-1-cyclopropoxyimino)-2-(2-tritylaminothiazol-4-yl)acetamidol-3-iodomethyl-3-cepem-4-carboxylate 1-oxide 14.2 g (14.7 mmol) of benzhydryl 7-[(Z)-2-(1-tert-butoxycarbonyl-1-cyclopropoxyimino)-2-(2-tritylaminothiazol-4-yl)acetamido]-3-chloromethyl-3-cephem-4-carboxylate was dissolved in 280 ml of methylene chloride, and 2.98 g (14.7 mmol) of m-chloroperbenzoic acid was added under cooling with ice. The mixture was stirred for 10 minutes. To the reaction solution, 60 ml of a 10% sodium thiosulfate aqueous solution was added. The solution was poured into a 5% sodium bicarbonate aqueous solution, and extracted with methylene chloride. The extract solution was dried over anhydrous sodium sulfate and concentrated under reduced pressure. The residue was dissolved in 300 ml of acetone, and 4.4 g (29.4 mmol) of sodium iodide was added at 0° C. The mixture was stirred at room temperature for 15 minutes. The reaction solution was washed with an aqueous sodium thiosulfate solution and with a saturated sodium chloride aqueous solution, and the organic solvent layer was dried over anhydrous sodium sulfate, and concentrated under reduced pressure. The residue was subjected to silica gel flush column chromatography (ethyl acetate/n-hexane =½) to obtain 9.52 g (yield: 60%) of the above identified compound.

(B) Benzhydryl 7-[(Z)-2-(1-tert-butoxycarbonyl-1-cyclopropoxyimino)-2-(2-tritylaminothiazol-4-yl)acetamido]-3-(6,7-dihydroxy-1,2,3,4-tetrahydroisoquinolin-2-yl)methyl-3-cephem-4-carboxylate 1-oxide 3.0 g (2.8 mmol) of the compound obtained in (A) was dissolved in 30 ml of dimethylformamide, and 0.85 g (3.3 mmol) of 6,7-dihydroxy-1,2,3,4-tetrahydroisoquinoline hydrobromide and 0.93 ml (6.6 mmol) of triethylamine were added thereto. The mixture was stirred at room temperature for 2 hours. The reaction solution was concentrated under reduced pressure, and the residue was subjected to silica gel flush column chromatography (ethyl acetate/n-hexane =3/1) to obtain 3.88 g of the above identified compound in an amorphous state (containing dimethylformamide).

NMR(DMSO-d$_6$)$\delta$: 1.40(13H, m), 5.08(1H, d, J=4 Hz), 5.90(1H, q, J=4.8), 6.32(1H, brs), 6.42(1H, brs), 6.84(1H, s), 6.97(1H, s)

(C) Benzhydryl 7-[(Z)-2-(1-tert-butoxycarbonyl-1-cyclopropoxyimino)-2-(2-tritylaminothiazol-4-yl)acetamido]-3-(6,7-dihydroxy-2-methyl-1,2,3,4,-tetrahydro-2-isoquinolinium)-methyl-3-cephem-4-carboxylate 1-oxide iodide 3.88 g of the compound obtained in (B) was dissolved in 38 ml (610 mmol) of methyl iodide, and left to stand at room temperature for 12 hours. Excess methyl iodide was distilled off under reduced pressure, and the residue was purified by silica gel column chromatography (5% methanol-methylene chloride) to obtain 3.2 g of the above identified amorphous compound (yield from step (B): 73%).

NMR(DMSO-d$_6$)$\delta$: 1.40(13H, m), 2.80(3H, brs), 5.18(1H, brs), 6.95(1H, m), 6.43(1H, brs), 6.58(1H, brs), 6.85(1H, s)

(D) Benzhydryl 7-[(Z)-2-(1-tert-butoxycarbonyl-1-cyclopropoxyimino)-2-(2-tritylaminothiazol-4-yl)acetamido]-3-(6,7-dihydroxy-2-methyl-1,2,3,4,-tetrahydro-2-isoquinolinium)-methyl-3-cephem-4-carboxylate iodide 3.2 g (2.54 mmol) of the compound obtained in (C) was dissolved in 32 ml of acetone, and 1.68 g (10.1 mmol) of potassium iodide was added thereto. Then, 0.36 ml (5.07 mmol) of acetyl chloride was dropwise added at −5° C., and the mixture was stirred for 1 hour. The reaction solution was poured into 170 ml of a 10% sodium metabisulfite aqueous solution, and then extracted with ethyl acetate. The extract solution was dried over anhydrous sodium sulfate, and the solvent was distilled off under reduced pressure to obtain the residue containing the above identified compound. The residue was employed for the subsequent reaction without purification.

(E) 7-[(Z)-2-(2-aminothiazol-4-yl)-2-(1-carboxy-1-cyclopropoxyimino)acetamido]-3-(6,7-dihydroxy-2-methyl-1,2,3,4-tetrahydro-2-isoquinolinium)methyl-3-cephem-4-carboxylate The residue obtained in (D) was dissolved in 6 ml of methylene chloride and 6 ml of anisole, and 15 ml of trifluoroacetic acid was added at 0° C. The mixture was stirred for 1 hour. The reaction solution was concentrated under reduced pressure, and ethyl acetate and water was added to the residue. The aqueous layer was separated. The organic layer was again extracted twice with water, and the aqueous layer thereby obtained was joined to the previous aqueous layer. The combined aqueous layer was concentrated, and purified by reversed column chromatography (ODS; LC-Sorb) to obtain 131 mg of the above identified compound (mixture of diastereomers A and B, yield from (D): 8%).

Melting point: 156° C. (decomposed)
IR(KBr): 3420, 1780, 1620 cm$^{-1}$
NMR(DMSO-d$_6$)$\delta$: 1.32 (4H, m), 2.80 (3H, brs), 4.95(1H, m), 5.40(1H, m), 6.2–6.3(1H, m), 6.35(1H, s), 6.84(1H, s), 8.04(1H, m)

EXAMPLE 18

(A) Benzhydryl 7-[(Z)-2-(1-benzhydryloxycarbonyl-1-cyclopentyloxyimino)-2-(2-tritylaminothiazol-4-yl)acetamido]-3-chloromethyl-3-cephem-4-carboxylate 2.12 g (3 mmol) of (Z)-2-(1-benzhydryloxycarbonyl-1-cyclopentyloxyimino)-2-(2-tritylaminothiazol-4-yl)acetic acid and 1.24 g (3 mmol) of benzhydryl 7-amino-3-chloromethyl-3-cephem-4-carboxylate were dissolved in 50 ml of methylene chloride, and 1.2 ml (9.6 mmol) of N,N-dimethylaniline was added under cooling with ice. Then, 0.29 ml (3.15 mmol) of phosphorus oxychloride was dropwise added thereto, and the mixture was stirred at the same temperature for 4 hours. 30 ml of chloroform and 30 ml of water was added to the reaction solution. The organic layer was washed with water and with a saturated sodium chloride aqueous solution, then dried over anhydrous sodium sulfate and concentrated to obtain the residue of the above identified compound, which was used for the subsequent reaction without purification.

(B) Benzhydryl 7-[(Z)-2-(1-benzhydryloxycarbonyl-1-cyclopentyloxyimino)-2-(2-tritylaminothiazol-4-yl)acetamido]-3-chloromethyl-3-cephem-4-carboxylate 1-oxide The residue obtained in (A) was dissolved in 50 ml of methylene chloride, and 710 mg (3.3 mmol) of m-chloroperbenzoic acid (purity: 80%) was added under cooling with ice. The mixture was stirred for 20 minutes. Then, 30 ml of methylene chloride and 40 ml of a 5% sodium bicarbonate aqueous solution were added to the reaction solution. The organic layer was separated and washed with water and with a saturated sodium chloride aqueous solution. The organic layer was dried over anhydrous sodium sulfate, and then concentrated to obtain the residue of the above identified compound, which was used for the subsequent reaction without purification.

(C) Benzhydryl 7-[(Z)-2-(1-benzhydryloxycarbonyl-1-cyclopentyloxyimino)-2-(2-tritylaminothiazol-4-yl)acetamido]-3-iodomethyl-3-cephem-4-carboxylate 1-oxide The residue obtained in (B) was dissolved in 40 ml of acetone, and 990 mg (6.6 mmol) of sodium iodide was added. The mixture was stirred at room temperature for 30 minutes. Then, 120 ml of ethyl acetate and 20 ml of a 5% sodium thiosulfate aqueous solution were added to the reaction solution for liquid separation. The organic layer was washed with water and with a saturated sodium chloride aqueous solution, then dried over anhydrous sodium sulfate and concentrated. The concentrated residue was subjected to silica gel flush column chromatography (ethyl acetate/n-hexane=½). The fraction containing the desired product was collected, and concentrated under reduced pressure, and isopropyl ether was added to the residue to obtain 2.92 g of a powder of the above identified compound (yield from A: 80.3%).

NMR(DMSO-d$_6$)$\delta$: 1.80(4H, m), 2.1(4H, m), 3.9(2H, m), 4.4(2H, m), 5.10(1H, d, J=5 Hz), 5.95(1H, dd, J=5&9 Hz), 6.77(1H, s), 6.80(1H, s), 7.35(35H, m), 8.5(1H, d, J=9 Hz), 8.8(1H, brs)

(D) Benzhydryl 7-[(Z)-2-(1-benzhydryloxycarbonyl-1-cyclopentyloxyimino)-2-(2-tritylaminothiazol-4-yl)acetamido]-3-(6,7-dihydroxy-1,2,3,4-tetrahydroisoquinolin-2-yl)methyl-3-cephem-4-carboxylate 1-oxide iodide 3 g (2.47 mmol) of the compound obtained in (C) was dissolved in 30 ml of dimethylformamide, and 913 mg (3.71 mmol) of 6,7-dihydroxy-1,2,3,4-tetrahydroisoquinoline hydrobromide and 1 ml (7.17 mmol) of triethylamine were added thereto at room temperature. The reaction solution was stirred for 40 minutes, and then dimethylformamide was distilled off under reduced pressure. Then, 80 ml of methylene chloride and 40 ml of water were added to the residue. The organic layer was dried over anhydrous sodium sulfate, and concentrated under reduced pressure. The residue was purified by silica gel flush column chromatography (10–30% acetone-methylene chloride) to obtain 3 g of a powder of the above identified compound (containing a certain amount of dimethylformamide).

IR(KBr): 1800, 1730, 1670, 1530, 1500, 1450, 1390, 1280, 1180 cm$^{-1}$

(E) Benzhydryl 7-[(Z)-2-(1-benzhydryloxycarbonyl-1-cyclopentyloxyimino)-2-(2-tritylaminothiazol-4-yl)acetamido]-3-(6,7-dihydroxy-2-methyl-1,2,3,4-tetrahydro-2-isoquinolinium)methyl-3-cephem-4-carboxylate 1-oxide iodide 3 g of the compound obtained in (D) was dissolved in 6 ml (96.3 mmol) of methyl iodide, and the solution was left to stand over night at room temperature. The reaction solution was concentrated under reduced pressure, and 40 ml of chloroform was added to the residue. The residue was dissolved and concentrated to obtain the above identified compound, which was used for the subsequent reaction without purification.

(F) Benzhydryl 7-[(Z)-2-(1-benzhydryloxycarbonyl-1-cyclopentyloxyimino)-2-(2-tritylaminothiazol-4-yl)acetamido]-3-(6,7-dihydroxy-2-methyl-1,2,3,4-tetrahydro-2-isoquinolinium)methyl-3-cephem-4-carboxylate iodide The residue obtained in (E) was dissolved in 66 ml of acetone, and 2.05 g (12.3 mmol) of potassium iodide was added thereto. Then, 0.44 ml (6.19 mmol) of acetyl chloride was dropwise added at −20° C., and the mixture was stirred at −10° C. for 1 hour. Then, the temperature was again adjusted to −20° C., and then 2.05 g (12.3 mmol) of potassium iodide and 0.44 ml of acetyl chloride were added, and the mixture was stirred at −10° for 1 hour. This operation was repeated twice. To the reaction solution, 240 ml of chloroform and 60 ml of water were added. The organic layer was washed with water, then dried over anhydrous sodium sulfate and concentrated to dryness to obtain the residue of the above identified compound, which was used for the subsequent reaction without purification.

(G) 7-[(Z)-2-(2-aminothiazol-4-yl)-2-(1-carboxy-1 cyclopentyloxyimino)acetamido]-3-(6,7-dihydroxy-2-methyl-1,2,3,4-tetrahydro-2-isoquinolinium)methyl-3-cephem-4-carboxylate The residue obtained in (F) was dissolved in 15 ml of methylene chloride and 1.5 ml of anisole, and 15 ml of trifluoroacetic acid was dropwise added under cooling with ice. The mixture was stirred at the same temperature for 2 hours, and then the solvent was distilled off under reduced pressure. To the residue, 80 ml of ether was added, and the precipitates were collected by filtration. The precipitates were added to 300 ml of water and stirred for 30 minutes. Insoluble matters were separated by filtration. The filtrate was purified by reversed silica gel column chromatography (ODS, 100 ml, 4% tetrahydrofuran-water), and freeze-dried to obtain 290 mg of the above identified compound (mixture of diastereomers A and B, yield from (D): 7.4%).

Melting point: 181° C. (decomposed)
IR(KBr): 1780, 1660, 1620, 1580, 1400, 1360 cm$^{-1}$
NMR(DMSO-d$_6$+TFA)$\delta$: 1.75(4H, brs), 2.1(4H, brs), 3.0(3H, brs), 2.9–4.8(10H, m), 5.4(1H, d, J=5 Hz), 5.95(1H, dd, J=5&8 Hz), 6.4(1H, brs), 6.65(1H, s), 7.17(1H, s)

EXAMPLE 19

In the same manner as in Example 14, 7-[(Z)-2-(2-aminothiazol-4-yl)-2-(1-carboxy-1-cyclobutoxyimiino)acetamide]-3-(6,7-dihydroxy-2-methyl-1,2,3,4-tetrahydro2-isoquinolinium)methyl-3-cephem-4-carboxylate was obtained.

Melting point: 182° C. (decomposed)
IR(KBr): 1780, 1670, 1620, 1530, 1390, 1350, 1280 cm$^{-1}$
NMR(DMSO-d$_6$)$\delta$: 1.90(2H, m), 2.4(4H, m), 2.95(3H, brs), 3.3–5.2(10H, m), 5.25(1H, d, J=5 Hz), 5.8(1H, dd, J=5&8 Hz), 6.55(1H, brs), 6.65(1H, s), 6.8(1H, d, J=8 Hz)

The compounds of the present invention are effective against Gram-negative bacteria, particularly against dextrose non-fermentative *Pseudomonas aeruginosa* or *Acinetobacter calcoaceticus*, and have a wide range of antibacterial spectrum. Thus, the compound of the present invention are expected to be an antibacterial agent

We claim:

1. A compound having the formula:

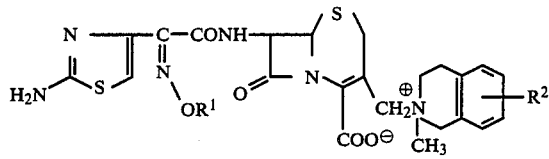

wherein $R^1$ is a straight chain, branched chain, or cyclic lower alkyl group which may be substituted by a carboxyl group, and $R^2$ designates vicinal dihydroxyl groups or diacetoxy groups; or a pharmaceutically acceptable salt, physiologically hydrolyzable ester or solvate thereof.

2. The compound according to claim 1, wherein $R^1$ is methyl, ethyl, n-propyl, isopropyl, n-butyl, carboxymethyl, 1-carboxy-1-methylethyl, cyclopropyl, cyclobutyl, cyclopentyl, cyclohexyl, 1-carboxy-1-cyclopropyl, 1-carboxy-1-cyclobutyl, 1-carboxy-1-cyclopentyl or 1-carboxy-1-cyclohexyl.

3. The compound according to claim 1, wherein the isoquinoline ring of the 2-methyl-1,2,3,4-tetrahydroisoquinolinium methyl in the formula is 5,6-dihydroxyisoquinoline, 6,7-dihydroxyisoquinoline, 7,8-dihydroxyisoquinoline, 5,6-diacetoxyisoquinoline, 6,7-diacetoxyisoquinoline or 7,8-diacetoxyisoquinoline.

4. The compound according to claim 1, which is 7-[(Z)-2-(2-aminothiazol-4-yl)-2-methoxyiminoacetamido]-3-(6,7-dihydroxy-2-methyl-1,2,3,4-tetrahydro-2-isoquinolinium)-3-cephem-4-carboxylate, 7-[(Z)-2-(2-aminothiazol-4-yl)-2-methoxyiminoacetamiido]-3-(6,7-diacetoxy-2-methyl-1,2,3,4-tetrahydro-2-isoquinolinium)methyl-3-cephem-4-carboxylate, 7-[(Z)-2-(2-aminothiazol-4-yl)-2-methoxyiminoacetamide]-3-5,6-dihydroxy-2-methyl-1,2,3,4-tetrahydro-2-isoquinolinium)methyl-3-cephem-4-carboxylate, 7-[(Z)-2-(2-aminothiazol-4-yl)-2-isopropoxyiminoacetamido]-3-(6,7-dihydroxy-2-methyl-1,2,3,4-tetrahydro-2-isoquinolinium)methyl-3-cephem-4-carboxylate, 7-[(Z)-2-(2-aminothiazol-4-yl)-2-carboxymethoxyimino) acetamido]-3-(6,7-dihydroxy-2-methyl-1,2,3,4-tetrahydro-2-isoquinolinium)methyl-3-cephem-4-carboxylate, 7-[(Z)-2-(2-aminothiazol-4-yl)-2-(1-carboxy-1-methyl-ethoxyimino)acetamide]-3-(6,7-dihydroxy-2methyl-1,2,3,4-tetrahydro-2-isoquinolinium)-methyl-3-cephem-4-carboxylate, 7-[(Z)-2-(2-aminothiazol-4-yl)-2-cyclopentyloxyiminoacetamido-]3-(6,7-dihydroxy-2-methyl-1,2,3,4-tetrahydro-2-isoquinolinium)methyl-3-cephem-4-carboxylate, 7-[(Z)-2-(2-aminothiazol-4-yl)-2-(1-carboxy-1-cyclopropoxyimino)acetamido]-3-(6,7-dihydroxy-2methyl-1,2,3,4-tetrahydro-2-isoquinolinium)methyl-3-cephem-4-carboxylate, 7-[(Z)-2-(2-amincthiazol-4-yl)-2-(1-carboxy1-cyclopenthyloxyimino) acetamido]-3-(6,7-dihydroxy-2-methyl-1,2,3,4-tetrahydro-2-isoquinolinium)methyl-3-cephem-4-carboxylate or 7-[(Z)-2-(2-aminothiazol-4-yl)-2-(1-carboxy-1-cyclobutoxyimino) acetamido]-3-(6,7-dihydroxy-2-methyl-1,2,3,4-tetrahydro-2-isoquinolinium)methyl-3-cephem-4-carboxylate, or a pharmaceutically acceptable salt, physiologically hydrolyzable ester or solvate thereof.

5. An antibacterial agent comprising an antibacterially effective amount of a compound having the formula:

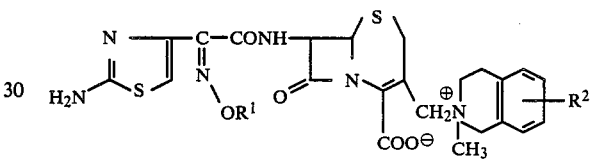

wherein $R^1$ is a straight chain, branched chain, or cyclic lower alkyl group which may be substituted by a carboxyl group, and $R^2$ designates vicinal dihydroxyl groups or diacetoxy groups; or a pharmaceutically acceptable salt, physiologically hydrolyzable ester or solvate thereof.

6. A method of treating disease caused by the infection of bacteria which comprises administering to a subject in need of treatment an antibacterially effective amount of the compound according to claim 1.

* * * * *